United States Patent
Hill et al.

(10) Patent No.: US 9,607,256 B2
(45) Date of Patent: Mar. 28, 2017

(54) AUGMENTING AND UPDATING DATA USING ENCRYPTED MACHINE-READABLE IDENTIFIERS

(71) Applicant: WonderHealth, LLC, Atlanta, GA (US)

(72) Inventors: Kenneth Hill, Atlanta, GA (US); Katherine S. Hill, Atlanta, GA (US)

(73) Assignee: WonderHealth, LLC, Atlanta, GA (US)

( * ) Notice: Subject to any disclaimer, the term of this patent is extended or adjusted under 35 U.S.C. 154(b) by 0 days.

(21) Appl. No.: 15/058,483

(22) Filed: Mar. 2, 2016

(65) Prior Publication Data

US 2016/0260003 A1  Sep. 8, 2016

Related U.S. Application Data

(60) Provisional application No. 62/127,404, filed on Mar. 3, 2015.

(51) Int. Cl.
| | |
|---|---|
| G06K 19/06 | (2006.01) |
| G06K 7/10 | (2006.01) |
| H04L 9/08 | (2006.01) |
| G06K 7/14 | (2006.01) |
| H04L 9/30 | (2006.01) |
| G06F 21/62 | (2013.01) |

(52) U.S. Cl.
CPC ... *G06K 19/06037* (2013.01); *G06F 21/6209* (2013.01); *G06K 7/10722* (2013.01); *G06K 7/1443* (2013.01); *H04L 9/0816* (2013.01); *H04L 9/30* (2013.01); *G06F 2221/2149* (2013.01)

(58) Field of Classification Search
CPC .................................................. G06K 19/06
See application file for complete search history.

(56) References Cited

U.S. PATENT DOCUMENTS

| | | |
|---|---|---|
| 6,523,116 B1 | 2/2003 | Berman |
| 6,802,005 B1 | 10/2004 | Berson |
| 6,854,651 B2 | 2/2005 | Smith |
| 7,387,249 B2 | 6/2008 | Hudson et al. |
| 7,519,825 B2 | 4/2009 | Geoffrey |
| 8,085,934 B1 | 12/2011 | Bhooma |

(Continued)

OTHER PUBLICATIONS

U.S. Appl. No. 15/058,366, filed Mar. 2, 2016.

(Continued)

*Primary Examiner* — Christle I Marshall
(74) *Attorney, Agent, or Firm* — Thomas | Horstemeyer, LLP

(57) ABSTRACT

Disclosed are various embodiments for augmenting and updating content data using encrypted machine-readable identifiers. A client application may be employed to transfer a first amount of data to a reader device using a first machine-readable identifier, where the reader device has access to at least one cryptographic key capable of decrypting the data. If the first amount of data is modified or augmented on the reader device, the client application may capture an image of a second machine-readable identifier generated by the reader device, decode and decrypt the machine-readable identifier to identify a second amount of data, and reconcile differences between the first amount of data and the second amount of data.

20 Claims, 17 Drawing Sheets

(56) References Cited

U.S. PATENT DOCUMENTS

| | | |
|---|---|---|
| 8,275,123 B2 | 9/2012 | Bichler et al. |
| 8,602,294 B2 | 12/2013 | Miller |
| 8,881,990 B2 | 11/2014 | Hunt et al. |
| 9,111,186 B2 | 8/2015 | Blasinski |
| 9,369,287 B1 | 6/2016 | Sarvestani |
| 2002/0060246 A1 | 5/2002 | Gobburu |
| 2004/0105542 A1 | 6/2004 | Takase et al. |
| 2004/0111601 A1 | 6/2004 | Racz |
| 2005/0132194 A1 | 6/2005 | Ward |
| 2006/0083404 A1 | 4/2006 | Shimosato |
| 2006/0144946 A1 | 7/2006 | Kuriyama |
| 2006/0161779 A1 | 7/2006 | Geoffrey |
| 2007/0102521 A1 | 5/2007 | Petersson |
| 2007/0107063 A1 | 5/2007 | Eckleder |
| 2007/0204162 A1 | 8/2007 | Rodriguez |
| 2009/0031139 A1 | 1/2009 | Geoffrey |
| 2009/0294539 A1 | 12/2009 | Kim |
| 2012/0045059 A1 | 2/2012 | Fujinami |
| 2012/0138679 A1 | 6/2012 | Doyle |
| 2012/0168497 A1* | 7/2012 | Yach ............... G06Q 10/107 235/375 |
| 2013/0054271 A1* | 2/2013 | Langford ............ G06Q 50/24 705/3 |
| 2013/0056535 A1 | 3/2013 | Rowlandson |
| 2013/0126601 A1 | 5/2013 | Lee |
| 2013/0173915 A1 | 7/2013 | Haulund |
| 2013/0179005 A1 | 7/2013 | Nishimoto |
| 2013/0185815 A1 | 7/2013 | Leotsarakos |
| 2013/0191640 A1 | 7/2013 | Bloomer |
| 2013/0231945 A1 | 9/2013 | Barry |
| 2013/0346302 A1 | 12/2013 | Purves et al. |
| 2014/0006051 A1 | 1/2014 | Vuong |
| 2014/0027504 A1 | 1/2014 | Ming |
| 2014/0059356 A1 | 2/2014 | Nesnow |
| 2014/0088983 A1 | 3/2014 | Neff |
| 2014/0122053 A1 | 5/2014 | Lotan |
| 2014/0142979 A1 | 5/2014 | Mitsunaga |
| 2014/0164016 A1 | 6/2014 | Evans |
| 2015/0019254 A1 | 1/2015 | Ibikunle et al. |
| 2015/0088674 A1* | 3/2015 | Flurscheim ........ G06Q 20/3276 705/17 |
| 2015/0100334 A1 | 4/2015 | Lin |
| 2015/0120423 A1 | 4/2015 | Farn |
| 2015/0186665 A1 | 7/2015 | Herring |
| 2016/0260003 A1 | 9/2016 | Hill |

OTHER PUBLICATIONS

International Search Report dated Jul. 26, 2016.
Non-Final Office Action mailed for U.S. Appl. No. 15/058,366 on Oct. 13, 2016.
Response to Non-Final Office Action for U.S. Appl. No. 15/058,366 filed on Dec. 27, 2016.

* cited by examiner

Capacity of 40-L Version Matrix Code

| Encoding Mode | Mode Indicator |
|---|---|
| Numeric | 7089 Characters |
| Alphanumeric | 4296 Characters |
| Byte | 2953 Characters |
| Kanji | 1817 Characters |

| Mode Name | Mode Indicator |
|---|---|
| Numeric | 0001 |
| Alphanumeric | 0010 |
| Byte | 0100 |
| Kanji | 1000 |
| ECI | 0111 |

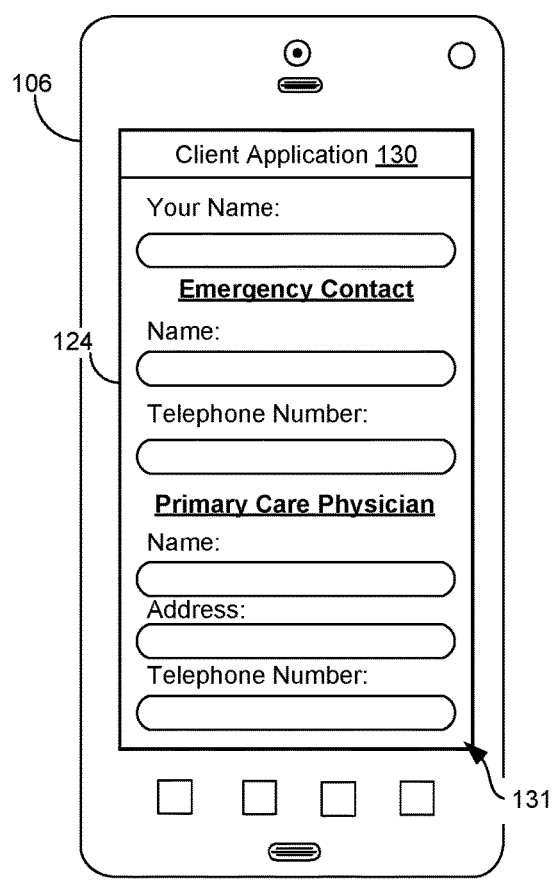 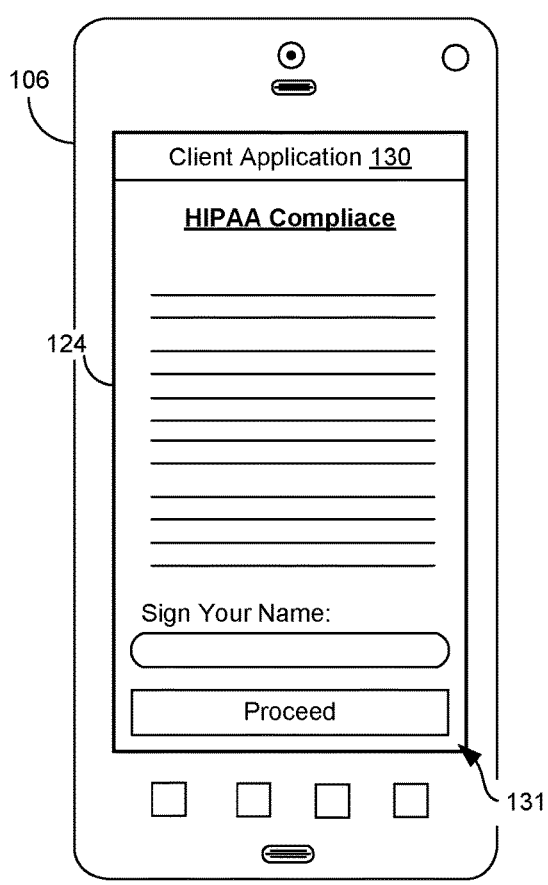
FIG. 7A     FIG. 7B

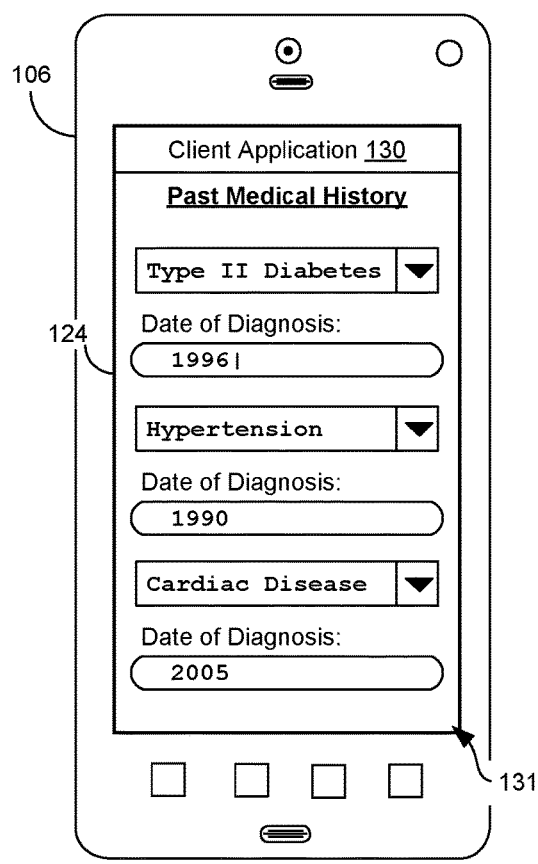 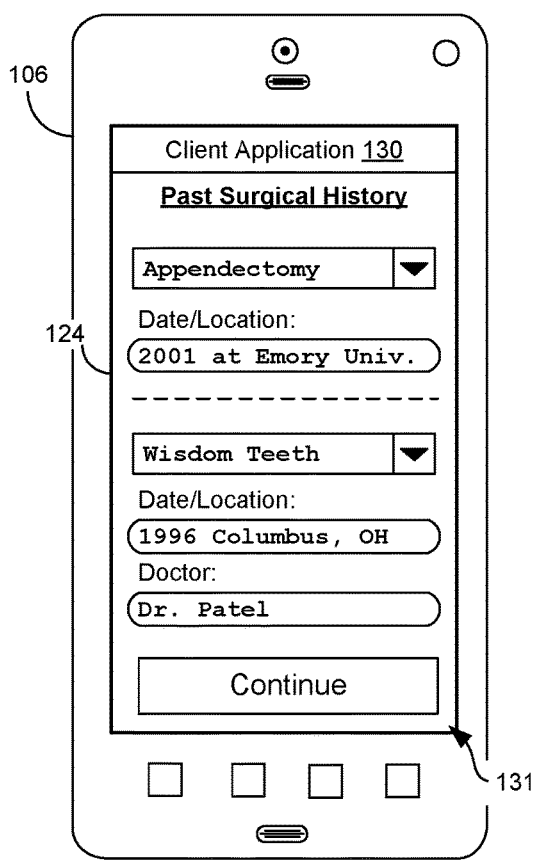
FIG. 7C  FIG. 7D

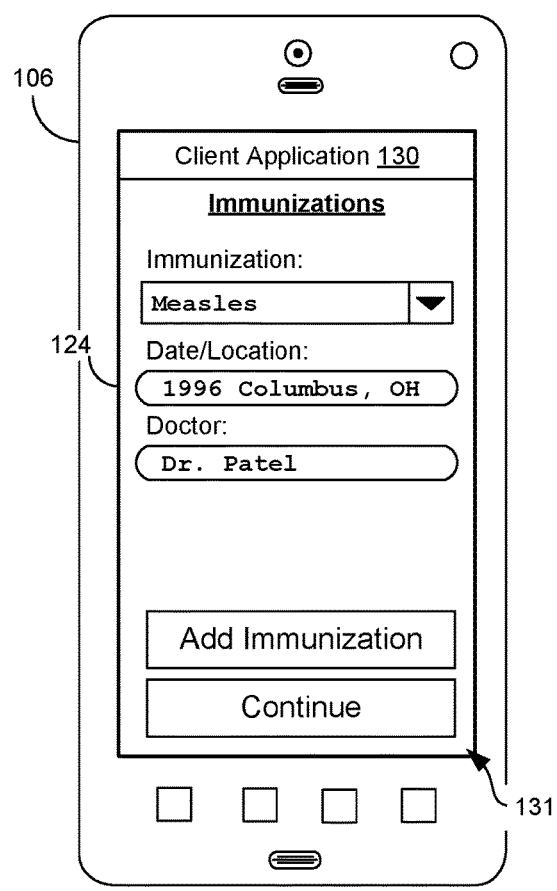 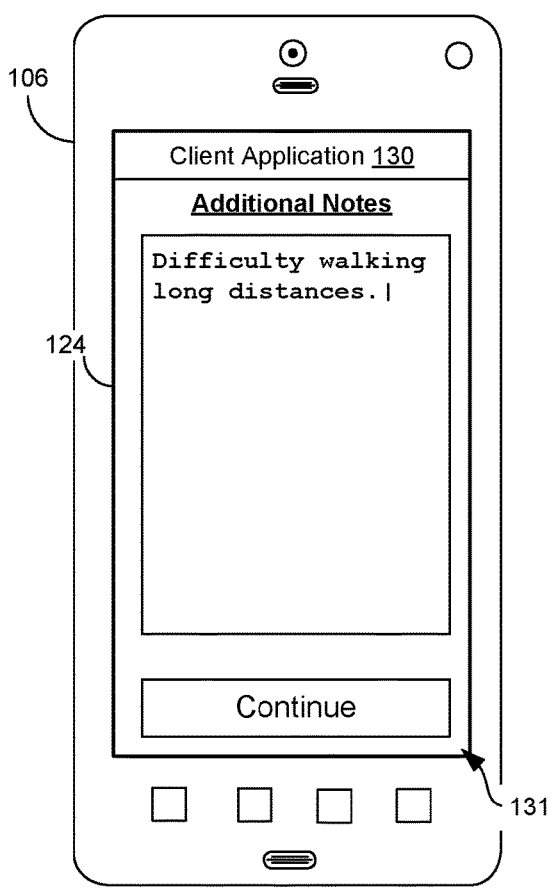
FIG. 7I  FIG. 7J

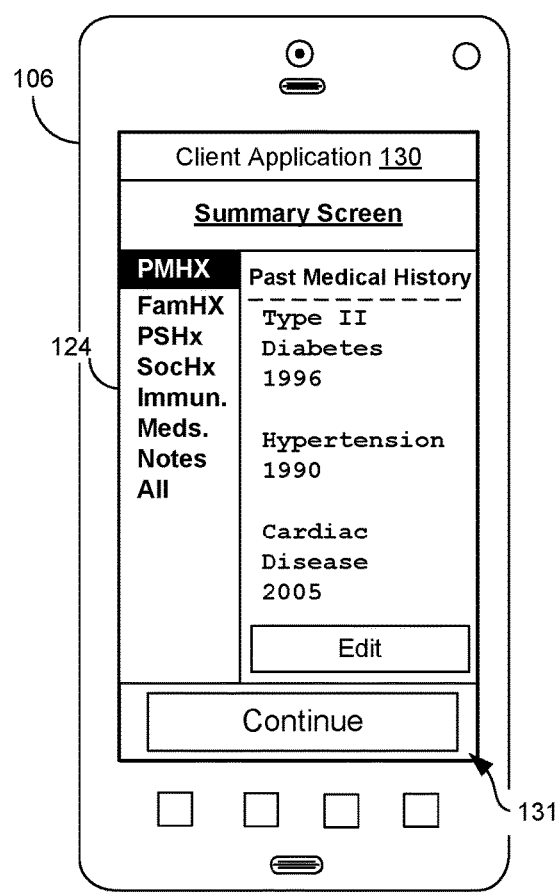
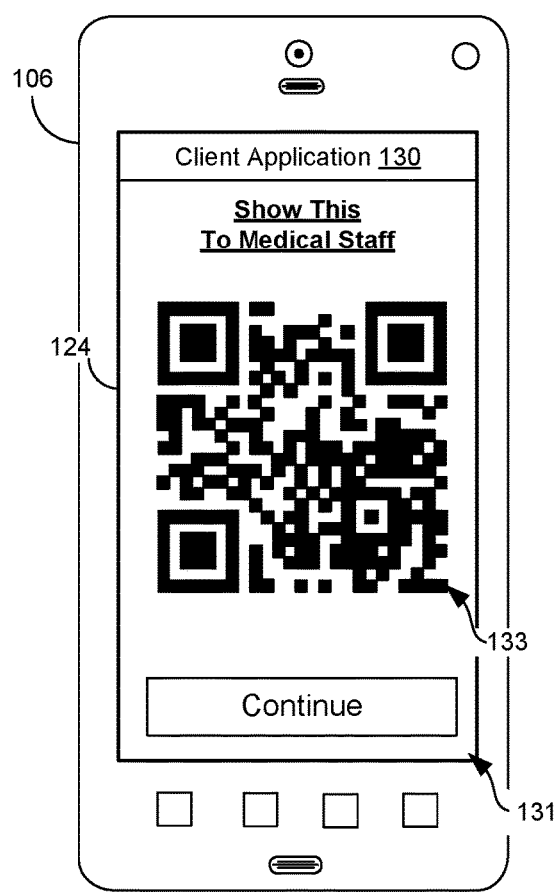
FIG. 7K  FIG. 7L

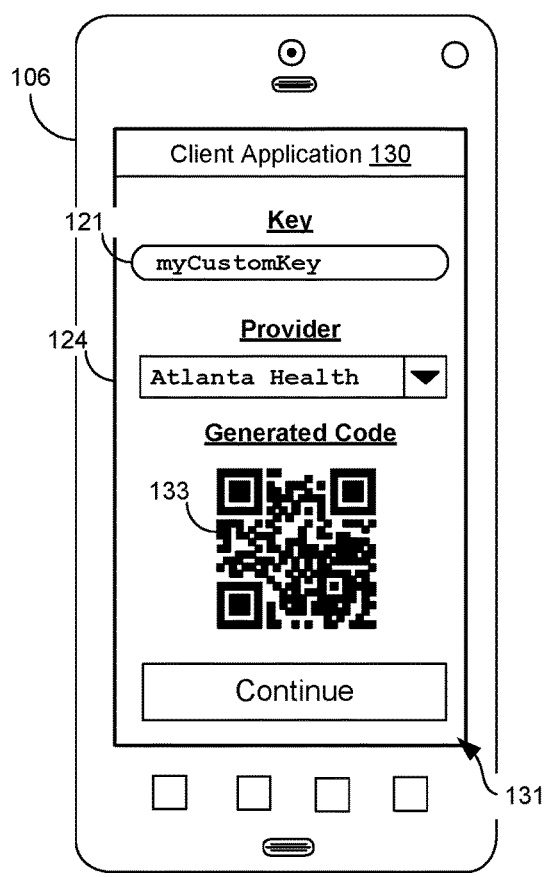 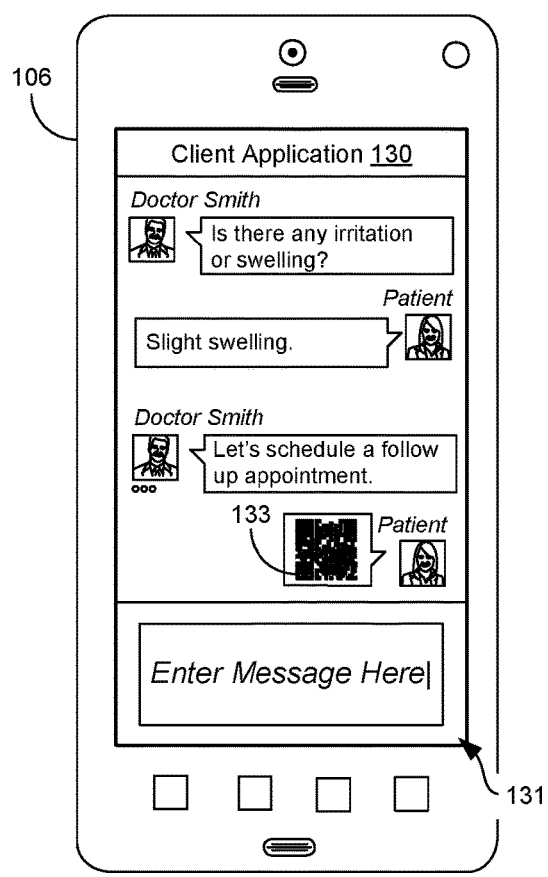
FIG. 7M   FIG. 7N

```
01    func generateMatrixCode() {
02        payloadData = getInputData();           // Get User Input from UI
03        key = getKey(receiverDevice);           // Get Key for Receiver Device
04        modeIndicator = "0010";                 // Alphanumeric Mode
05        charCount = sizeOf(payloadData);        // Get Char Size of Payload Data
06        encryptedData = encrypt(payloadData, key); // Encrypt Payload Data
07        error = calculateError(encryptedData);  // Reed Solomon Error Code
08        a = formatData(modeIndicator, charCount,
09                       encryptedData, error);   // Format Data
10        return generateMatrixImage(a);          // Matrix Code Image
11    }
```

FIG. 8

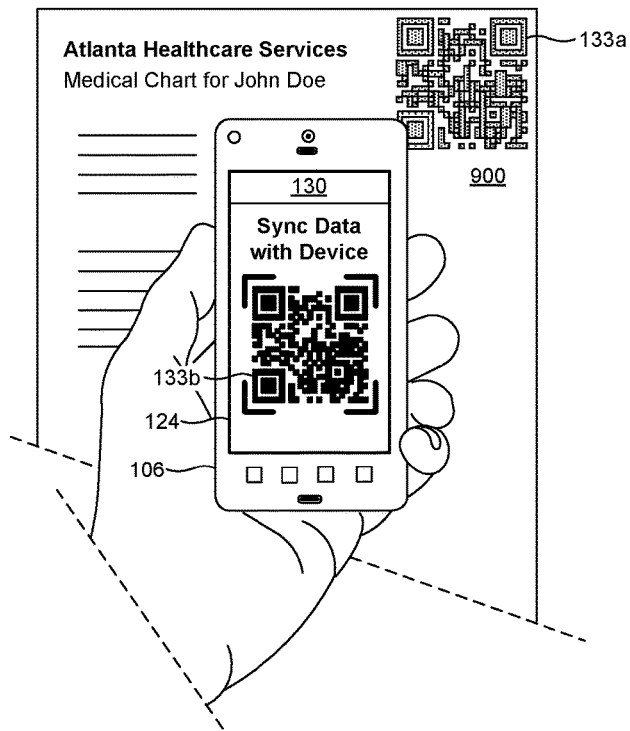

FIG. 9

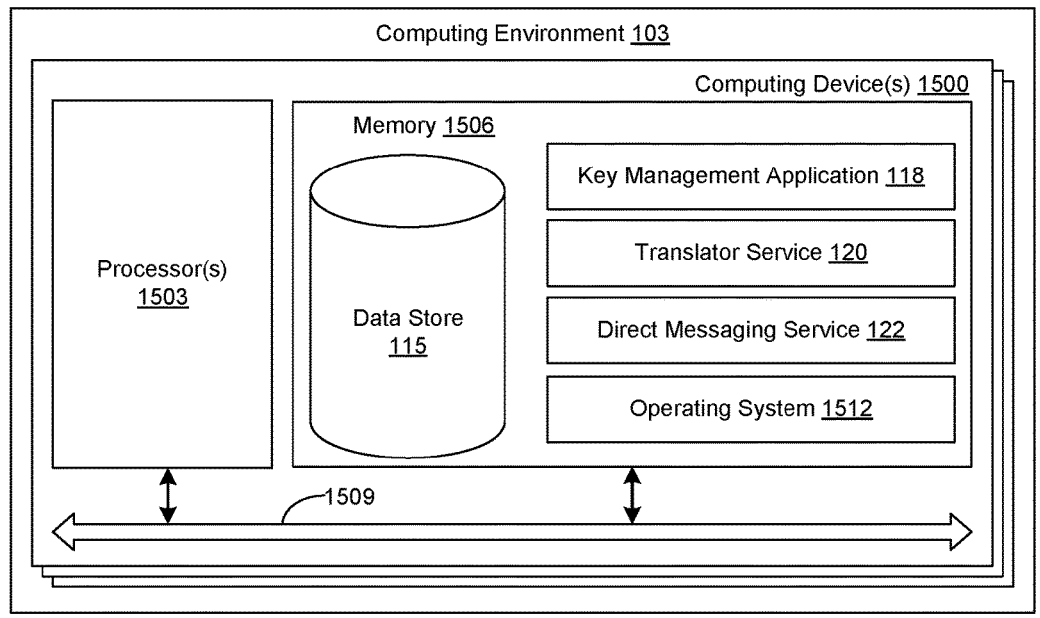
FIG. 15
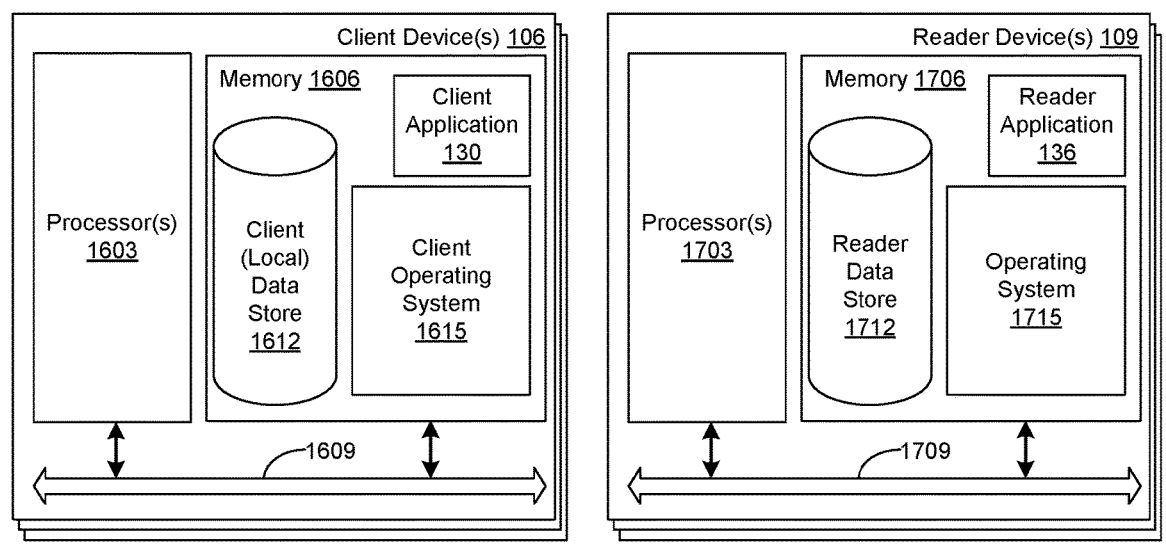
FIG. 16  FIG. 17

AUGMENTING AND UPDATING DATA USING ENCRYPTED MACHINE-READABLE IDENTIFIERS

CROSS-REFERENCE TO RELATED APPLICATIONS

This application claims the benefit of and priority to U.S. Provisional Patent Application No. 62/127,404, entitled "GENERATING IDENTIFIER WITH ENCODED HEALTH INFORMATION," filed on Mar. 3, 2015, the contents of which are hereby incorporated by reference in its entirety herein. This application is related to U.S. patent application Ser. No. 15/058,366, entitled "ACCESS CONTROL FOR ENCRYPTED DATA IN MACHINE-READABLE IDENTIFIERS," filed on Mar. 2, 2016, the contents of which are hereby incorporated by reference in its entirety herein.

BACKGROUND

Machine-readable identifiers can be employed to format data in a medium recognizable by a reader device, such as a barcode or a matrix code scanner. However, any person having a suitable reader can obtain the data embodied in the machine-readable identifier unless the underlying data is encrypted. Managing which devices have access to encrypted data in machine-readable identifiers remains problematic.

FIELD OF THE INVENTION

The present disclosure relates to cryptography, machine-readable identifier technology, data security, and, to a certain degree, computer vision.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIG. 8 is pseudocode that illustrates one example of code used to configure a computing device or a client device to generate a machine-readable identifier according to various embodiments.

FIG. 9 shows an example of updating or augmenting data on a client device using a machine-readable identifier generated by another device according to various embodiments.

FIGS. 15-17 are schematic block diagrams that provide example illustrations of a computing environment, a client device, and a reader device employed in the networked environment of FIGS. 1 and 2 according to various embodiments.

DETAILED DESCRIPTION

Figure 1:
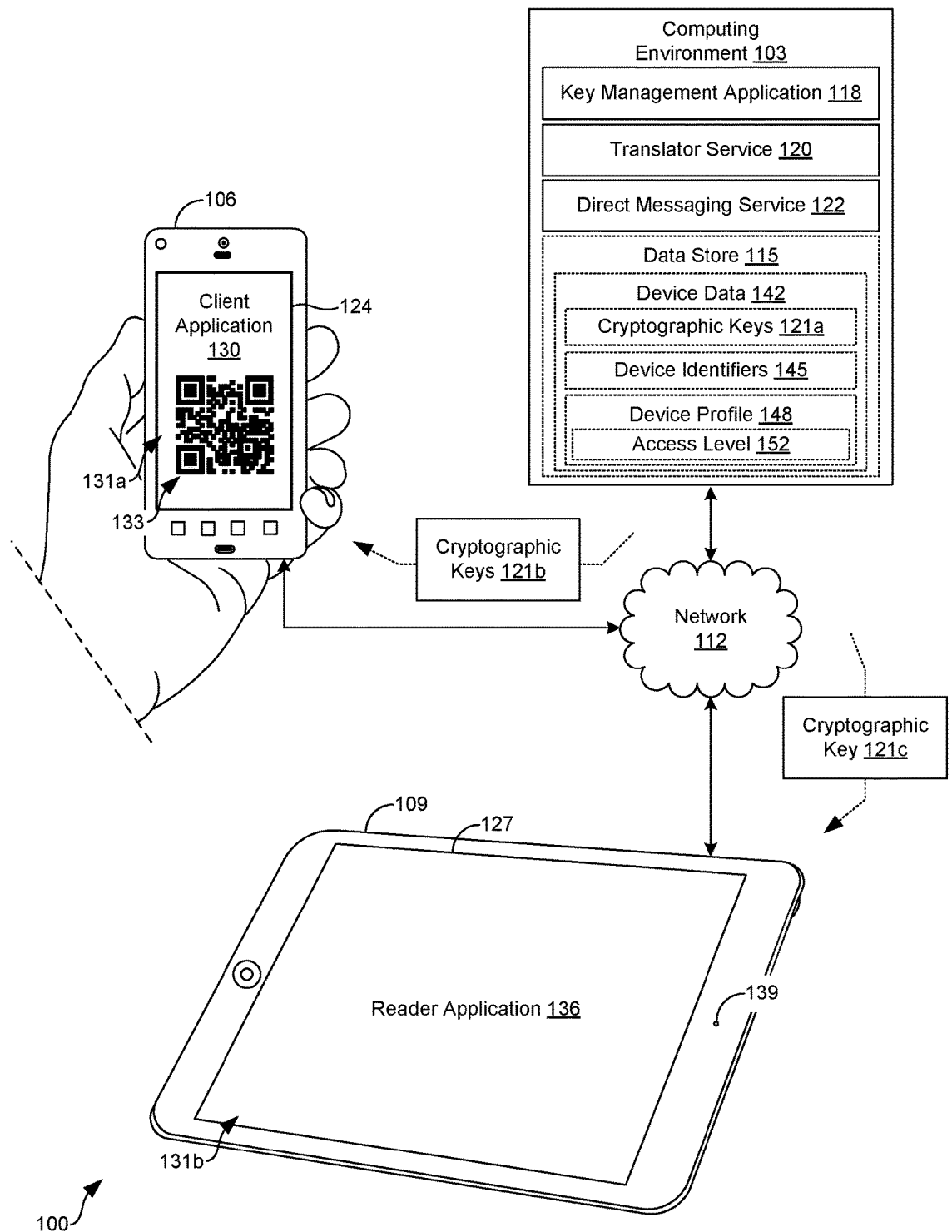
FIG. 1 shows an example of a networked environment for providing access control to information collected by a client application according to various embodiments.

The present disclosure relates to access control for segmented data in machine-readable identifiers. Machine-readable identifiers, such as barcodes, matrix codes, or other similar identifiers, can be employed to format data in a medium recognizable by a reader device, such as a barcode or a matrix code scanner. While machine-readable identifiers can be used to transfer data from one device to another without the use of a wired or wireless network, any person having a suitable reader can obtain the data embodied in the machine-readable identifier unless the underlying data is encrypted. As the underlying data may be sensitive, a user may want to control which portions of the underlying data is capable of being read by various devices.

For example, in some embodiments, medical information can be encoded in a machine-readable identifier. People are required at times to produce sensitive data that the person may wish to keep private, such as providing a medical history during a visit to a medical office. The medical history, as well as other personally identifying information, is generally required by chiropractors, holistic medicine providers, veterinarians, urgent or emergency medicine centers, dentists, insurance companies, etc. Family members may bear the responsibility of providing such information to healthcare providers on behalf of their relatives if they are not capable of doing so.

While a person may want to provide his or her general practitioner with a complete medical history, the person may not want to provide the complete medical history to another provider, such as a chiropractor or a dentist. Instead, they may wish to limit the data to what is relevant for the medical care professional. Accordingly, in various embodiments, a single machine-readable identifier may be encoded with data where different devices are capable of reading different portions of the data. For example, a person may authorize his or her general practitioner to obtain a complete medical history from a matrix code while a chiropractor, using the same matrix code, may only be able to obtain a subset of the medical history as authorized by a user.

According to various embodiments, a user may use his or her electronic device, such as a smartphone or tablet, to provide medical intake information, as opposed to the standard practice of filling out medical forms using pen and paper. As medical, personal, and other delicate information provided by the user via the electronic device may be sensitive, sending the information over a network raises concerns. For example, the information could be intercepted using packet sniffing software or rogue access points. Further, databases where the information is stored can be hacked. As such, machine-readable identifiers, such as bar codes or matrix codes, can be used to transfer information between nearby devices without the use of a network.

Machine-readable identifiers, however, usually rely on open source or transparent standards making interpretation of data embodied in the machine-readable identifiers susceptible to unauthorized access. For example, if medical information was embedded in a matrix code, any commercially-available matrix code reader may be able to obtain the medical information. While the underlying data can be encrypted, only devices having access to a suitable key can decrypt the data. However, sharing a single key among multiple devices deters a person from providing a complete amount of information as the person may be aware that all devices with the key are capable of accessing their information.

Accordingly, in embodiments described herein, access control for segmented data in machine-readable identifiers may be provided. In one embodiment, a client application executable on a client device may be configured to receive a first cryptographic key associated with a first device profile and a second cryptographic key associated with a second device profile over a network. The client application may facilitate the collection of input data from a user through an ingestion process which can include a series of user interfaces that prompt the user to enter a variety of data. Once received, the client application may segment or otherwise format the input data into at least a first portion of data and a second portion of data. For example, the first portion of data may be capable of being interpreted by a reader device for a general practitioner while the second portion of data may be capable of being interpreted by a reader device for a chiropractor.

The client application may encrypt the first portion of data using the first cryptographic key and the second portion of data using the second cryptographic key. A remote application, referred to herein as a key management application, may execute in a remote computing device, such as server, and oversee the transmission and receipt of keys capable of decrypting the data, as authorized by the user. Alternatively, in other embodiments, a receiver device may be associated with a key in the remote computing environment. The remote application can provide the client application with a key for a receiver device, such that the information is encrypted for access by the receiver device. Finally, the client application may generate a machine-readable identifier using the first portion of data as encrypted and the second portion of data as encrypted for rendering in a display accessible by the client device. The receiver device can capture one or more images of the machine-readable identifier to access the underlying data using automated image analysis and computer vision.

As a non-limiting example, a user of the client application may associate his or her general practitioner with a high level of access, where the general practitioner is able to use his or her device to access all of the input data provided by the user of the client application. The key management application can send a key to the device for the general practitioner as well as to the device for the user. Similarly, the key management application can send a key to the device for the chiropractor or other medical provider and to the device for the user. The client application may encode data authorized for receipt by the general practitioner using a corresponding key while encoding data authorized for receipt by the chiropractor using a different key for the chiropractor. To this end, using a single machine-readable identifier, access control to the underlying data of the machine-readable identifier is provided.

As may be appreciated, a technical problem exists for transferring sensitive data between devices without the use of a network as many ways of intercepting data transmitted over a network exist. Additionally, a technical problem exists there are many ways that network stored data (data stored on a network device) can be obtained without authorization. Accordingly, the embodiments described herein solve the technical problem by presenting ways of transmitting sensitive data between devices without the use the network to transmit and receive the sensitive data.

Although this disclosure provides multiple examples in context of healthcare data, the embodiments enclosed herein are applicable across many industries. Additionally, this disclosure provides examples in context of matrix codes and other similar machine-readable identifiers. However, in some embodiments, visual image recognition may be employed to identify data encoded in different forms of images, such as employed in the Clickable Paper™ applications marketed by RICOH®.

In the following discussion, a general description of the system and its components is provided, followed by a discussion of the operation of the same.

With reference to FIG. 1, shown is a networked environment 100 according to various embodiments. The networked environment 100 includes a computing environment 103, a client device 106, and a reader device 109, which are in data communication with each other via a network 112. In various embodiments, the client device 106 and the reader device 109 may not communicate any information from one device to another over the network 112 beyond cryptographic keys, as will be discussed. The network 112 includes, for example, the Internet, intranets, extranets, wide area networks (WANs), local area networks (LANs), wired networks, wireless networks, or other suitable networks, etc., or any combination of two or more such networks. For example, such networks may comprise satellite networks, cable networks, Ethernet networks, and other types of networks.

The computing environment 103 may comprise, for example, a server computer or any other system providing computing capability. Alternatively, the computing environment 103 may employ a plurality of computing devices that may be arranged, for example, in one or more server banks, computer banks, or other arrangements. Such computing devices may be located in a single installation or may be distributed among many different geographical locations. For example, the computing environment 103 may include a plurality of computing devices that together may comprise a hosted computing resource, a grid computing resource and/or any other distributed computing arrangement. In some cases, the computing environment 103 may correspond to an elastic computing resource where the allotted capacity of processing, network, storage, or other computing-related resources may vary over time.

Various applications and/or other functionality may be executed in the computing environment 103 according to various embodiments. Also, various data is stored in a data store 115 that is accessible to the computing environment 103. The data store 115 may be representative of a plurality of data stores 115 as can be appreciated. The data stored in the data store 115, for example, is associated with the operation of the various applications and/or functional entities described below.

The components executed on the computing environment 103, for example, may include a key management application 118, a translator service 120, a direct messaging service 122, and other applications, services, processes, systems, engines, or functionality not discussed in detail herein. The key management application 118 may be executed to oversee the transmission and receipt of various cryptographic keys 121a . . . 121c stored in the data store 115, as will be discussed.

The translator service 120 may be executed to translate user input from a first language, such as Spanish, to a second language, such as English. In some embodiments, the translator service 120 may be used to translate a question stored in the computing environment 103 for use in an ingestion process from a first language to a second language.

The direct messaging service 122 can be employed to send encrypted direct messages over the network from a client device 106 to another. In one embodiment, an application executable on the client device 106 encrypts a message generated by a user of the client device 106 and sends the encrypted message to the direct messaging service 122 over the network 112 which then transmits the encrypted message to a recipient client device 106. In one example, the direct messaging service 122 permits a patient to communicate directly with his or her health provider. In other embodiments, messages may be passed between client devices 106 using a machine-readable identifier, as will be discussed.

In further embodiments, the computing environment 103 can include applications or services that provide for cloud-based storage of encrypted information, such as encrypted health information, although in other embodiments, encrypted information may not be stored in the computing environment 103.

The client device 106 is representative of a plurality of client devices that may be coupled to the network 112. The client device 106 may comprise, for example, a processor-based system such as a computer system. Such a computer system may be embodied in the form of a desktop computer, a laptop computer, personal digital assistants, cellular telephones, smartphones, set-top boxes, music players, web pads, tablet computer systems, game consoles, electronic book readers, smartwatches, or other devices with like capability. The client device 106 may include a client device display 124 and the reader device 109 may include a reader device display 127. The client device display 124 and the reader device display 127 may comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc.

The client device 106 may be configured to execute various applications such as a client application 130 and/or other applications. The client application 130 may be executed in the client device 106, for example, to perform an ingestion process, whereby a series of user interfaces 131a are rendered in the client device display 124 to prompt the user for user input. In one example, one or more questions are provided to the user to obtain personal information, medical information, or other suitable information. The one or more questions may be obtained from the computing environment 103 or hardcoded in the client application 130.

The client application 130 may encrypt the user input and generate a machine-readable identifier 133 with the encrypted user input. As may be appreciated, the reader device 109 uses a reader application 136 to interpret the machine-readable identifier 133 and access the encrypted user input. Using one or more cryptographic keys 121, the reader application 136 can decrypt the encrypted user input for local storage on the reader device 109 or for remote storage.

In some embodiments, the client application 130 and the reader application 136 may comprise, for example, a browser, a dedicated application, etc., and the user interface 131a generated by the client application 130 or the user interface 131b generated by the reader application 136 may comprise a network page, an application screen, etc. The client device 106 may be configured to execute applications beyond the client application 130 such as, for example, email applications, social networking applications, word processors, spreadsheets, and/or other applications.

The reader device 109 may include a front-facing imaging device 139 or a rear-facing imaging device (not shown), such as a camera or other device capable of interpreting the machine-readable identifier 133. The reader application 136 may be executed in the reader device 109 to capture one or more images of the machine-readable identifier 133 generated by the client application 130. Similarly, the client device 106 may comprise one or more imaging devices, such as a front-facing or rear-facing camera. In various embodiments, the reader application 136 is further executed to decrypt the encrypted user input obtained from the machine-readable identifier 133 and present the health information in the reader device display 127.

The reader application 136 may be configured to maintain versions of data provided by the user and generate a suitable interface that facilitates navigating between particular types of data or different versions. While the client application 130 may be configured to abstain from transmitting medical or other types of information over the network 112, in some embodiments, the reader application 136 may communicate data to a remote or cloud-based service, such as a HIPAA-compliant electronic health record system. While the client application 130 may not send health or other types of information over the network 112, the computing environment 103 may backup or store versions of the machine-readable identifier 133 in the data store 115. When a user upgrades or replaces his or her client device 106, the machine-readable identifier 133 can be used to populate data on the new client device 106.

The data stored in the data store 115 may include device data 142 as well as other data as can be appreciated. The device data 142 may include information associated with one or more client devices 106 and reader devices 109. In one example, each reader device 109 may be associated with a unique cryptographic key 121 where the key management application 118 sends the cryptographic key 121 to the client application 130. The client application 130 can then generate a machine-readable identifier 133 that includes user input data encrypted with the cryptographic key 121 for the reader device 109. As the reader device 109 also maintains a copy of its cryptographic key 121, it is able to decrypt and interpret the user input data.

In another example, each client device 106 may be associated with one or more cryptographic keys 121 where the key management application 118 sends the cryptographic keys 121 to the reader devices 109 at the instruction of a user of the client application 130. The client application 130 can generate a machine-readable identifier 133 that includes user input data encrypted with the one or more cryptographic keys 121. The key management application 118, at the instruction of the user of the client application 130 for example, can send a cryptographic key 121 to the reader device 109 so that it can decrypt and interpret the user input data.

The device data 142 may include device identifiers 145 that uniquely identify a client device 106 or a reader device 109. The device data 142 may further include device profiles 148 which, in turn, may include access levels 152. In some embodiments, a user of the client application 130 can associate certain reader devices 109 with particular access levels 152. In one example, a person can associate a first reader device 109 for his or her general practitioner with a first level of access and a second reader device 109 for his or her dentist with a second level of access. To this end, the user of the client application 130 can designate which data is accessible by which reader device 109 based on the level of access. As will be described, the user input can be segmented or partitioned by information available to each reader device 109. To this end, the reader application 136 may provide differing levels of access to the information specified by the user or predetermined by the computing environment 103.

The cryptographic keys 121 may include a numeric, binary, or alphanumeric string used to encrypt data. In various embodiments, the cryptographic keys 121 may comprise symmetric cryptographic keys 121, asymmetric cryptographic keys 121, or a combination thereof.

Figure 2:
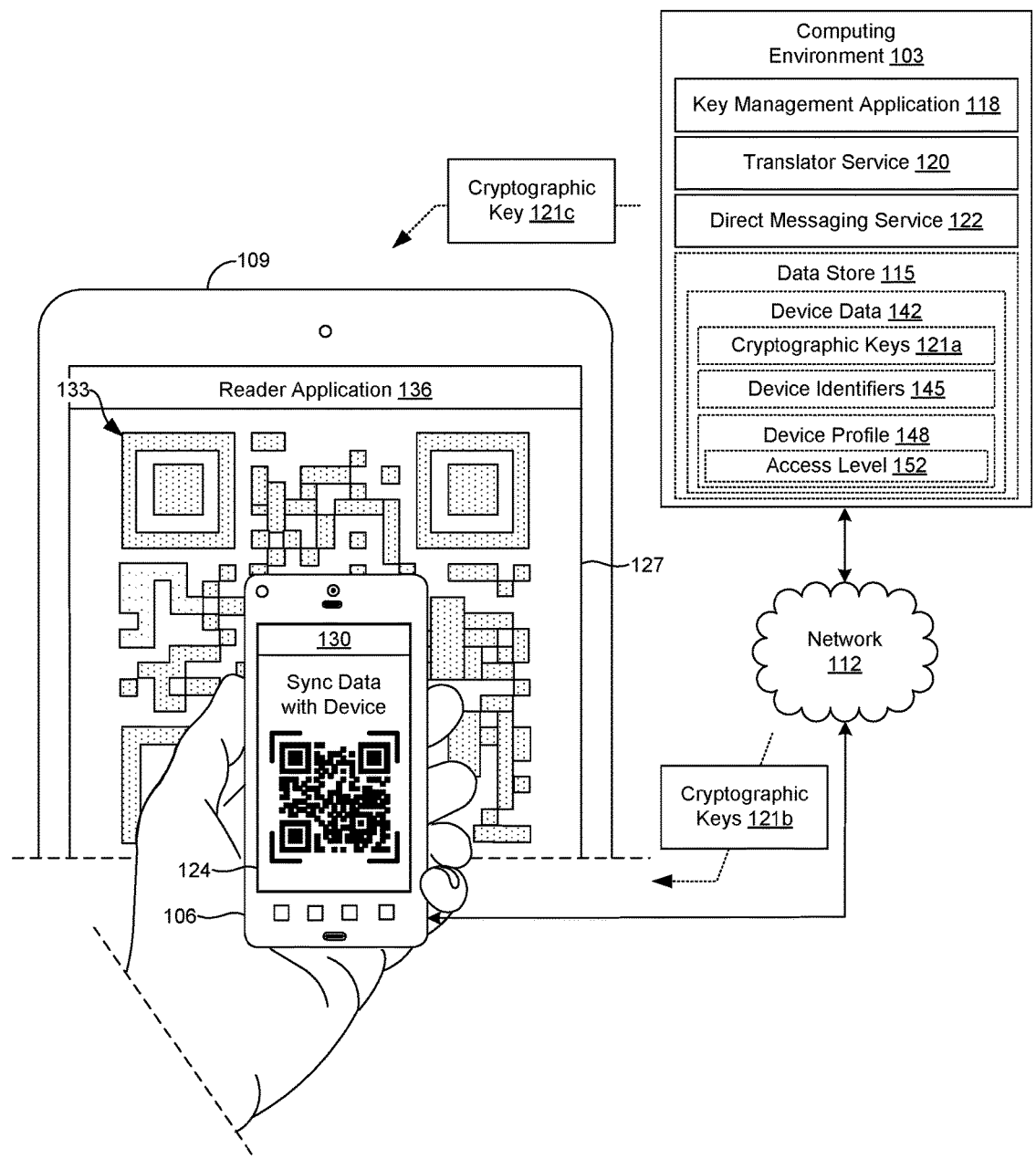
FIG. 2 shows another example of a networked environment for augmenting and updating content data using encrypted machine-readable identifiers according to various embodiments.

With reference to FIG. 2, shown is another example of the networked environment 100 according to various embodiments. In some circumstances, the input data provided by the user of the client application 130 may be manipulated on the reader device 109 or other device with access to the decrypted information. For example, a doctor may alter data provided the user to include up-to-date blood pressure, weight, or other information. The user may wish to store this information on his or her client device 106 to maintain a more complete and accurate medical history.

To this end, in some embodiments, the reader application 136 may utilize its cryptographic key 121 (or other cryptographic key 121 available to the client device 106) to provide the client device 106 with updated, modified, supplemented, or otherwise manipulated data. The client application 130 can facilitate the capture of one or more images of the machine-readable identifier 133 generated on the reader device 109 and rendered in the reader device display 127.

In various embodiments, the underlying data of the machine-readable identifier 133 generated by the reader application 136 is encrypted using a cryptographic key 121 only available to the client device 106 and the reader device 109. The client application 130 can decrypt the underlying data and store the data locally on the client device 106. If the user performs parts of ingestion process, the updated data may be provide in automatically populated fields in the user interface 131. By scanning the machine-readable identifier 133 and having suitable cryptographic keys 121 to access the underlying data, the reader application 136 may update locally stored data and may interface with other applications, such as scheduling applications, appointment management applications, medication refill applications, or EHR applications, to update information associated therewith.

Figure 3:
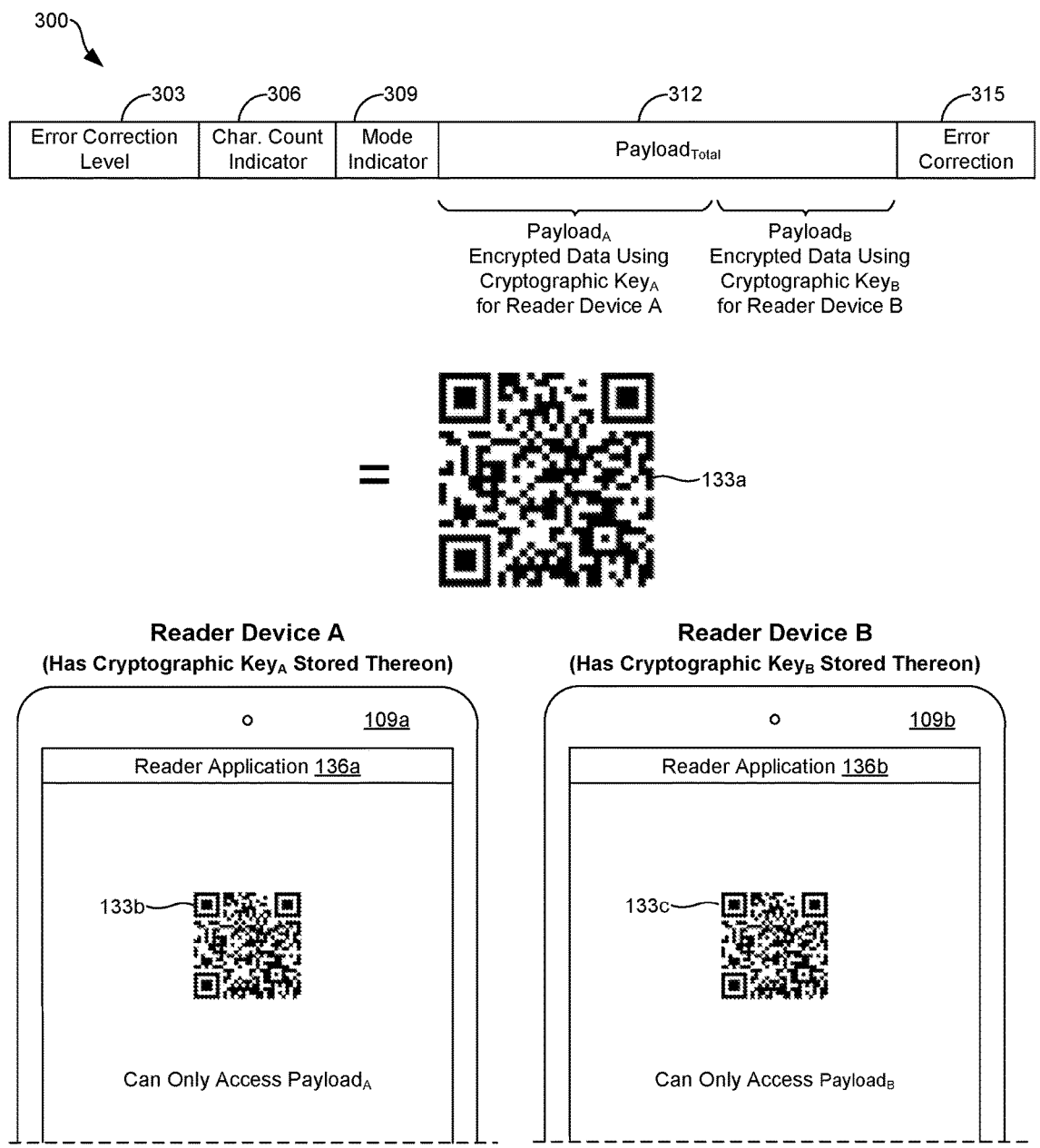
FIG. 3 shows a data structure used to generate a machine-readable identifier having portions of data encrypted using multiple keys according to various embodiments.

Referring next to FIG. 3, shown is an example of a data structure 300 comprising data used to generate an image of the machine-readable identifier 133a . . . 133c. The data structure 300 may include, for example, an error correction level 303, a character count indicator 306, a mode indicator 309, a payload 312, an error correction 315, and/or other data as may be appreciated.

Matrix codes, also referred to as quick response (QR) codes, traditionally employ Reed-Solomon error correction which is used to generate error correction codewords (bytes) based on the encoded data. A reader application 136a . . . 136b can use these error correction level 303 to determine whether the data was read incorrectly and, if so, correct the errors in the data using the error correction codewords. For matrix codes, there are four levels of error correction levels 303 designated as L, M, Q, and H with error correction capabilities of 7%, 15%, 25%, and 30%, respectively.

Figures 4, 5, 6:
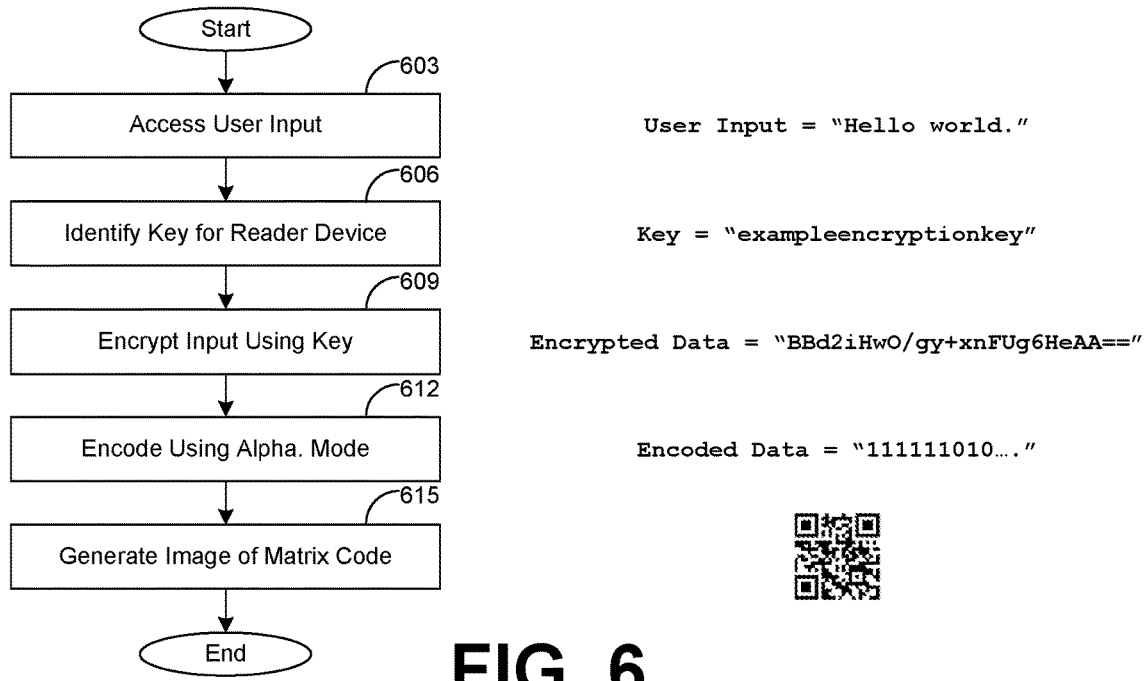
FIG. 4 includes a table that illustrates the capacity of a 40-L version matrix code.
FIG. 5 includes a table that illustrates the mode indicator bits for a mode of encoding data.
FIG. 6 is a flowchart illustrating one example of encrypting and encoding data for use in a machine-readable identifier according to various embodiments.

Matrix codes have different sizes, and a matrix code of a particular size is referred to as a version. There are forty versions available although additional versions are possible and are included within the scope of the disclosure. For example, version 1 is the smallest version of a matrix code, and is 21 pixels by 21 pixels in size. Each version is 4 pixels larger than the previous version. Version 4 is the largest version, and is 177 pixels by 177 pixels. The largest version has the highest capacity of characters, as shown in the table of FIG. 4.

The payload 312 can be encoded according to different modes as set by the mode indicator 309. The mode indicator 309 may comprise a four-bit string, as shown in FIG. 5. The encoded data may start with the appropriate mode indicator that states the mode being used for the subsequent bits. The largest version of matrix code has the highest capacity of characters, as shown in the table of FIG. 4. The character count indicator 306 includes the number of characters that are being encoded.

To generate the machine-readable identifier 133, the client application 130 (or the reader application 136) may access the user input received during the ingestion process and encrypt the data using a cryptographic key 121. In embodiments where the cryptographic key 121 is asymmetric, RSA or other suitable encrypting algorithm may be employed. In embodiments where the cryptographic key 121 is symmetric, the Advanced Encryption Standard (AES) or other suitable encrypting algorithm may be employed. The encrypted user input may be encoded according to the mode indicator 309. For example, assuming the encrypted user input is a string of alphanumeric characters, the mode indicator 309 may be set to 0010. Alphanumeric encoding may include breaking up a string into pairs and creating a binary number for each pair.

The data intended for a first reader device 109a may be encrypted using a cryptographic key 121 accessible by the first reader device 109a (shown in FIG. 3 cryptographic key 121A) and encoded as payload$_A$. Similarly, the data intended for a second reader device 109b may be encrypted using a cryptographic key 121 accessible by the second reader device 109b (shown in FIG. 3 cryptographic key 121B) and encoded as payload$_B$. When scanned by a reader device 109, only a portion of the payload$_{Total}$ may be interpreted by the reader device 109.

Referring next to FIG. 6, shown is a flowchart that illustrates the transformation of input data into a matrix code or other machine-readable identifier 133. Starting with step 603, user input is accessed. The user input may include, for example, health information, emergency contact information, or other type of information obtained during the ingestion process or from a user interface 131 presented by the client application 130. In the example of FIG. 6, a string of user input includes "Hello world" for explanatory purposes.

In step 606, a cryptographic key 121 is identified based on a reader device 109 for which the data is intended. For example, a user can specify a particular portion of his or her medical history intended for his or her general practitioner. A cryptographic key 121 for one or more reader devices 109 for the general practitioner may be identified. In step 609, the user input is encrypted using the cryptographic key 121 identified in 606. Using AES encryption and the key of "exampleencryptionkey," a string of encrypted data includes "BBd2iHwO/gy+xnFUg6HeAA=="

Next, in step 612, the encrypted data is encoded using alphanumeric mode or other suitable mode, such as numeric, byte, Kanji, or ECI. For the first two characters "BB" in the encrypted data, a binary number is generated using alphanumeric coding to obtain "111111010." This may continue until all of the encrypted data is encoded using a suitable mode. Finally, in step 615, the image of the matrix code is generated using the encoded data as the payload according to the matrix code standard.

In various embodiments, the AES-256 encryption algorithm may be employed to encrypt the underlying data. An initialization vector (IV) or starting variable (SV) may be employed for use by a mode that randomizes the encryption and produces distinct ciphertexts, even if the same plaintext is encrypted multiple times. (AES CBC Pkcs7). Some modes, such as Electronic Codebook (ECB) and Cipher Block Chaining (CBC), may require that the final block be padded before encryption, so suitable padding may be employed.

In an embodiment where AES-256 is employed, a cryptographic key 121 may include 256 bits (32 bytes) with an IV of 128 bits (16 bytes). The IV may be randomly generated on each encryption performed by the client application 130 or the reader application 136 to provide a distinct encryption result (different from previous encryptions), even if the data to be encrypted has not changed. The generated IV may be stored with the encrypted data locally on the client device 106 or the reader device 109 allowing for future decryption, as discussed herein.

In some embodiments, the encrypted data is stored locally on the client device 106 or the reader device 109 in association with a password, biometric data, or a PIN code. Additionally, each user, or entity for which data is provided (e.g., patient, relative, pet) may have his or her own cryptographic key 121 (i.e., encryption key). As a result, any data encrypted on a specific device can only be decrypted on that device when the suitable password, biometric data, or PIN code is provided.

As the AES encryption algorithm requires a cryptographic key 121 and an IV to encrypt or decrypt data, the IV may be stored in association with the encrypted data to be successfully decrypted at a future time. In some embodiments, the key management service 115 manages the storage and transmission of the IV to the client devices 106 or reader devices 109 along with the cryptographic key 121. The IV key may comprise 16 bytes or other suitable length. In some embodiments, IV key may be split up and stored in predefined locations along the cryptographic key 121. For example, a first number of bytes of the IV key may be placed at a first location in the cryptographic key 121 while a second number of bytes of the IV key may be placed at a second location in the cryptographic key 121, and so forth. The IV key may be removed from the cryptographic key 121 before the cryptographic key 121 is used. This feature adds an extra level of security in the encrypted data. For example, even if the cryptographic key 121 is intercepted, successfully guessed by brute force, etc., without knowing how to retrieve the IV out of the data, it will be difficult, if not impossible, to decrypt the encrypted data.

FIGS. 7A-7N show various examples of user interfaces 131 of the client application 130 used to perform an ingestion process by prompting the user with various types of user input. As may be appreciated, prior to performing the ingestion process, the user may be required to provide a username, a password, biometric information, or other information to properly authenticate the user of the client device 106. In FIG. 7A, an exemplary home screen for the client application 130 is shown where the user may input primary information for an individual. This may not include medical information, but information for identification purposes. This may be used to identify a name of the individual (e.g., the owner, dependent, pet, or other individual).

Subsequently, the client application 130 may prompt the user to input basic information, such as date of birth, emergency contact information, primary care physician contact information, or other basic information. Also the user interface 131 may permit a user to change the individual for which information is provided. For example, the user may change the individual from himself or herself to another individual, such as a child, dependent, pet, etc. These secondary profiles will also have data fields to place information for primary care physicians, emergency contact information, medical history, etc.

FIG. 7B shows an embodiment of a Health Insurance Portability and Accountability Act (HIPAA) compliance and documentation user interface 131. From this user interface 131, information pertaining to various regulations, such as HIPPA, is shown followed by a suitable explanation to obtain requisite consent. In various embodiments, a link or other user interface component may be generated that causes another application, such as a browser application, to show information for those needing further explanation as to the specifics of compliance. Following review, a prompt may be made for an electronic signature and a date or timestamp to verify that the user has reviewed the material and obtain requisite consent.

Turning now to FIG. 7C, a user interface 131 illustrates one embodiment of the screen dedicated to obtaining past medical information for an individual. The user interface 131 of FIG. 7C enables a user to provide medical diagnoses that they have been given in the past by a medical professional. In various embodiments, smart text, auto-population, dropdown suggestions, and/or other similar components may be included to facilitate a correct spelling of the most common ailments and/or diseases. The client application 130 may also obtain data relating to the date at which this diagnosis was given. These may then be placed in numerical order based on the dates. In the event a diagnosis is not listed, a free text option may be available. An additional text box may be created for additional information that may be important.

FIG. 7D shows a user interface 131 in which past surgical information can be obtained by prompting the user to provide all previous surgical experiences. As noted above, in various embodiments, smart text, auto-population, dropdown suggestions, and/or other similar components may be included to facilitate a correct spelling of the most common surgeries or medical procedures. The date and institution of these surgical procedures may also be obtained, if known. Surgical procedures will then be placed in temporal order with associated data fields for date and institution where the procedure was performed. In the event that a procedure is not listed, an option for free text will be available.

Figure 7E:
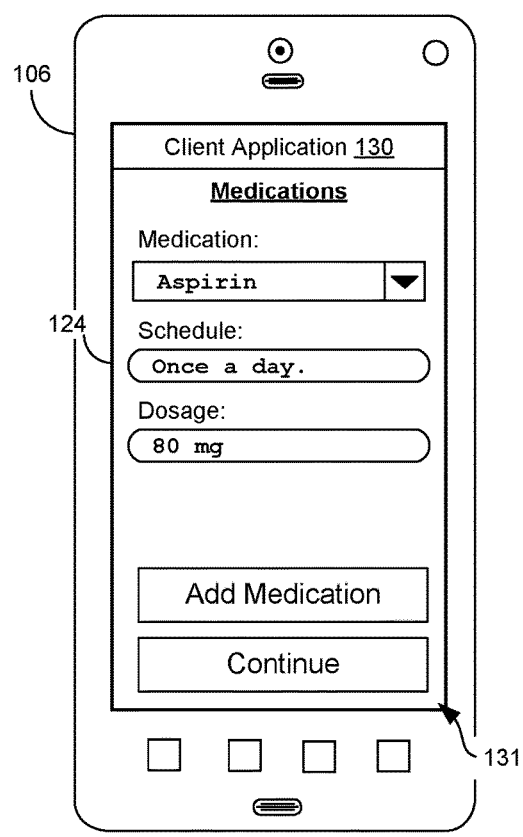
FIGS. 7A-7N show various examples of user interfaces generated by a client application according to various embodiments.

Referring next to FIG. 7E, a user interface 131 illustrating an embodiment of a screen dedicated to obtaining current and past medications is shown which enables the user to provide current and previous medications. In various embodiments, smart text, auto-population, dropdown suggestions, and/or other similar components may be included to facilitate a correct spelling of the most common medications. The date when the provided medication was started, the reason for the medication, and the dose and frequency of administration may be included. In the case that this is an old medication that the user is no longer taking, a field for date when the medication was stopped will be included with a reason why it was discontinued. In the case that a medication is not listed, an option for free text will be available.

Figure 7F:
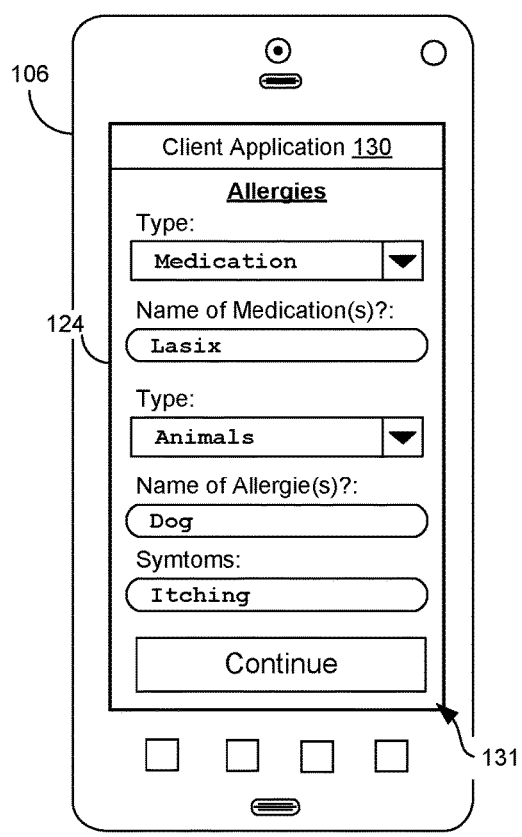

FIG. 7F shows a user interface 131 where a user can provide current and past allergies, medications, environmental triggers, animals, and other relevant information. In various embodiments, smart text, auto-population, dropdown suggestions, and/or other similar components may be included to facilitate a correct spelling of the most common medications and allergens. The type of reaction to the allergen will also be included. These will be placed in numerical order with associated field for type of reaction to each allergen.

Figure 7G:
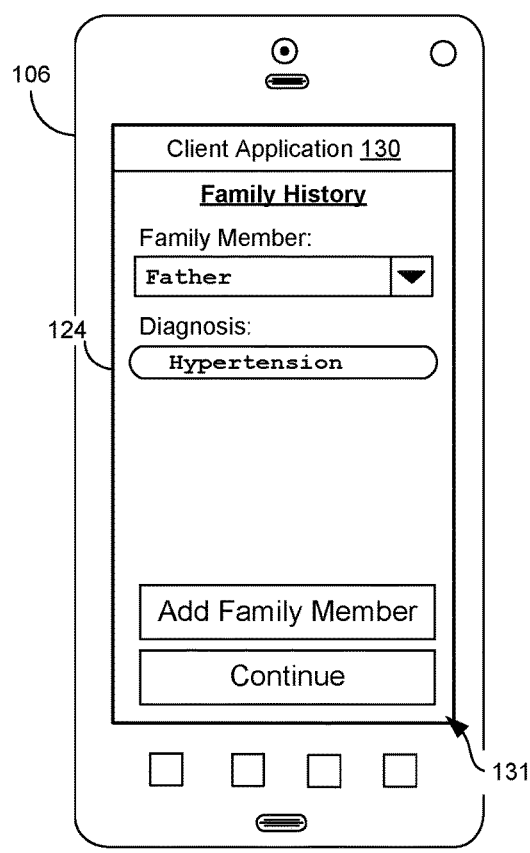

In the non-limiting example of FIG. 7G, a user interface 131 is shown that enables a user to provide information associated with her or her family medical history. In some embodiments, the user may be presented with specific common medical conditions to advise whether it is applicable to the family medical history. Suitable data fields may be used for uncommon diseases. Further, smart text, auto-population, dropdown suggestions, and/or other similar components may be included to facilitate a correct spelling of common ailments or diseases. The user may also characterize which family member possessed this diagnosis with their age and year of "deceased," if applicable.

Figure 7H:
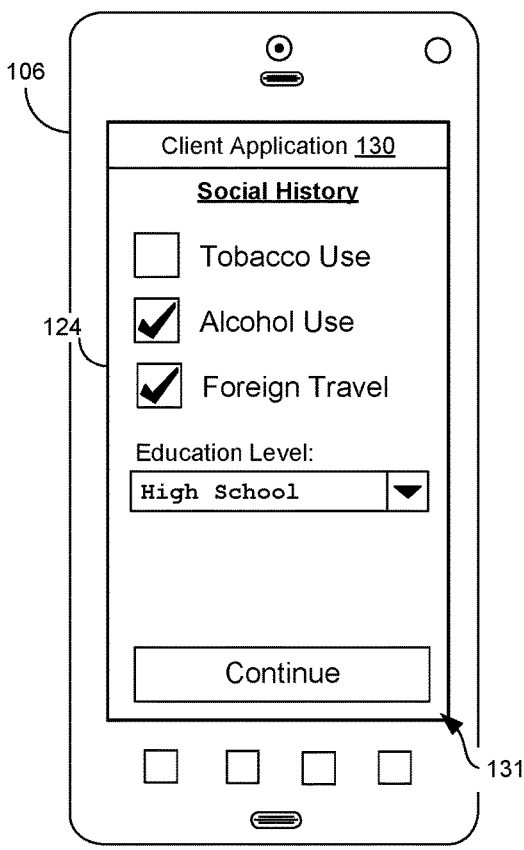

FIG. 7H illustrates an embodiment of a user interface 131 dedicated to obtaining a social history from a user. For example, a user may be presented with a form to provide information associated with an individual's social history. In some embodiments, the form includes data fields covering tobacco history, alcohol use, foreign travel, education level, etc. This may also include specific pediatric information such as fellow home inhabitants, firearms in the home, pets in the home, lead and tuberculosis exposure, etc., based on the age calculated from the date of birth provided earlier.

Referring next to FIG. 7I, a user interface 131 illustrates one embodiment that obtains immunizations from a user. Smart text may be employed to assist the user in correctly spelling immunizations. Open text fields can be provided for immunizations that are not commonly given as may be needed for foreign travel. In some embodiments, the date that the immunization was provided may be a required field. This information may be placed in chronological order based on the date of immunization.

FIG. 7J shows an embodiment of a user interface 131 that enables a user to provide miscellaneous notes with can be retained locally only for access by the user or can be included in the machine-readable identifier 133. For example, notes may include a reminder regarding a specific healthcare encounter. In various embodiments, this may be limited to 100 characters or other suitable amount as this is not a list of symptoms but just a reminder for a specific visit. As with any other section, the notes page can be left blank if there is no need to update this information. In some embodiments, the data provided in the notes field can be excluded from the data of the machine-readable identifier 133.

FIG. 7K shows another drawing of the client device 106 generating a user interface 131 in the client device display 124. In the non-limiting example of FIG. 7K, an embodiment is shown where a user is provided with information previously provided by the user. As may be appreciated, in embodiments where health information is obtained, information pertaining to one or more of the eleven organ systems may be ideally acquired. The user interface 131 may facilitate printing or transferring information packets to a physician or other interested person in a format predefined by the user, an administrator, or a format specified by a healthcare provider. This provides the ability to correlate this information in a format that is preferred by physicians and legible for both the owner and the physician. In other examples, the user interface 131 may receive information associated with a patient's pharmacy, insurance, or other related subjects. The ingestion process may include a review of body systems as well as health screenings.

Further, the client application 130 may organize information provided during the ingestion process in a predefined format. In one example, the information can be sorted chronologically and by subject, such as allergies or medications. For embodiments in which the information is medical data, the chronological format, common to healthcare providers, provides a way to efficiently present the data obtained using the client application 130. It will provide all the health information designated as required by the healthcare provider. Because the provided information may be complete and accurate, it may assist in limiting medical errors by correct identification of medications and allergies, as well as providing the entirety of the medical history that may prove to be necessary to the physician or provider.

The data may be formatted and/or compressed prior to encryption by the client application 130, or the reader application 136 may format the data when decrypted and/or decompressed. Accordingly, either the client application 130 or the reader application 136 may format the data into a predefined format, such as the Clinical Document Architecture (CDA) format which includes a flexible markup standard developed by Health Level 7 International. The CDA format includes a predefined structure of certain medical records, such as discharge summaries and progress notes to exchange information between patients and medical professionals. The CDA format permits the inclusion of text, images, and other types of multimedia, such as audio or video. In other examples, the format can be specified by the health care provider via the reader application 136.

In various embodiments, the client application 130 may export a summary of the information into a Microsoft Word®, PDF®, or other suitable format for a user to print at the office of a healthcare provider or prior to the visit. In some embodiments, the machine-readable identifier 133 may be positioned in the corner of the generated document or in another suitable location. Using a reader device 109, the healthcare provider can scan the machine-readable identifier 133 from the client device display 124 or a document to import this information into a chart or electronic health record (EHR), depending on customs of the particular practice. As may be appreciated, a reader device 109 for the healthcare provider may be capable of decrypting information provided by the machine-readable identifier 133, as the client application 130 may be configured to encrypt the health information prior to generating the machine-readable identifier 133. As a result, a user of the client application 130 can bypass the lengthy process of filling out medical intake forms, for example, while sitting in an office. As the information provided by the user can be updated by the medical professional, it may aid in limiting medical errors by correct identification of medications and allergies, as well as providing the entirety of the medical history that may prove to be necessary to the physician.

The client application 130 may include a mobile application or a web-based application accessed via a browser application. Individuals who use the web-based application may be able to convert the summary information into a Word® or PDF® format for the owner to print prior to the visit and the information may be deleted upon completion of a session. In the corner of the printout, the associated machine-readable identifier 133 can be shown.

Based on the discretion and capabilities of the healthcare provider, another embodiment specifies that the client application 130 generates an email with an attachment of the information and/or the machine-readable identifier 133 to email and share electronically with the healthcare provider, office staff, or health system. This can be completed by the owner either from home prior to the visit or while in the waiting room of the healthcare provider. The format of the information will be that which is preferred by the healthcare provider. From this point it can be printed to add to the patient's paper chart, scanned or manually input into the electronic medical record. Finally, it may be electronically linked to an EHR or proprietary electronic medical record (EMR) system. Prior to sharing this information electronically, the owner may be required again to review HIPAA regulations and for an electronic signature and date/time stamp for review of this information.

Turning now to FIG. 7L, a machine-readable identifier 133 having the user input provided during the ingestion process may be shown. By holding the encrypted image up to a lens or camera of a reader device 109, the encrypted health information may be transferred for interpretation by the reader device 109. In some embodiments, a dependent may transfer his or her information to the client device 106 of a parent, or vice versa, by capturing an image of the machine-readable identifier 133. The key management application 118 facilitates the transfer of the suitable cryptographic keys 121 when requisite consent is obtained.

With reference to FIG. 7M, a user of the client application 130 can specify the cryptographic key 121 and a recipient of the data, such as an owner of a reader device 109 or a different client device 106. In other embodiments, the cryptographic key 121 can be pseudo-randomly generated by the client application 130 or the key management application 118. If generated by the client application 130, the cryptographic key 121 is transmitted to the key management application 118 which, in turn, communicates the cryptographic key 121 to a reader device 109 or other client device 106 as instructed by a user of the client application 130. For example, the user of the client device 106 may have the cryptographic key 121 transmitted to one or more reader devices 109 associated with the "Atlanta Health" provider. In other embodiments, a predefined cryptographic key 121 is used based on the selection of the provider. For example, the key management application 118 may store one or more cryptographic keys 121 for the "Atlanta Health" provider. When "Atlanta Health" is selected, the client application 130 may use the one or more cryptographic keys 121 stored in association with the "Atlanta Health" provider to encrypt information for use in a machine-readable identifier 133.

In further embodiments, the cryptography key 121 may be set as a date of birth, social security number, or other constant that may not be widespread or publicly available. Any healthcare providers that obtain required software necessary to read and transfer the information represented in the encrypted QR image may then be permitted to instantaneously extract the user input electronically and wirelessly.

In some embodiments, an additional layer of security may be employed where the recipient of the information may be required to enter in another identifier specific to the originating user, such as a date of birth or social security number, before the information will be decrypted.

The process of extracting the information may be accomplished by holding the machine-readable identifier 133 to a camera lens of the reader device 109 or another client device 106 in possession by a healthcare provider or other interested person. As can be appreciated, this can be performed by personnel in a front office and in a minute or less. The obtained information can then be used by the reader application 136 or other applications on the reader device 109 to add to a patient's paper chart or an electronic medical record system. Additionally, the reader application 136 may be configured to automatically populate fields in third-party EMR systems.

Referring next to FIG. 7N, the client application 130 may facilitate sending encrypted messages from a client device 106 to another. In one example, the client application 130 permits a patient to communicate directly with his or her health provider. The client application 130 may encrypt a message generated by a user of the client device 106 and send the encrypted message to the direct messaging service 122 over the network 112. The direct messaging service 122 may then transmit the encrypted message to a recipient client device 106. In other embodiments, messages may be passed between client devices 106 using a machine-readable identifier 133. The client application 130 may further facilitate the transmission of the machine-readable identifier 133 through the direct messaging service 122.

Turning now to FIG. 8, shown is pseudocode 800 that may be implemented in configuring the client application 130, the reader application 136, or other appropriate application to generate a matrix code or other type of machine-readable identifier 133. For example, a function in Line 01 of the pseudocode may be programmatically called to generate a matrix code. Line 02 receives the user input to be included in the machine-readable identifier 133, such as user input provided in the ingestion process performed by presenting the user interfaces 131 of FIGS. 7A-7K. As the user input is stored locally on the client device 106, it can be appropriately queried.

In Line 03, a cryptographic key 121 is obtained using an appropriate function call. In the embodiment of FIG. 8, the cryptographic key 121 is obtained based on an identifier provided for a particular reader device 109. For example, a user of the client application 130 can specify the intended recipient of the data. In other embodiments, the user may specify his or her own cryptographic key 121. In further embodiments, the cryptographic key 121 may be pseudo-randomly generated or determined using a date of birth, social security number, or other information provided by the user.

In Line 04, a mode indicator 309 is established. In the example of FIG. 8, the mode indicator is set to "0010" which indicates alphanumeric mode. In Line 05, the character count of the input data is determined. In Line 06, a function call is made to an appropriate function that encrypts the user input using the cryptographic key 121, returning an encrypted string or other suitable variable type. In Line 07, a Reed-Solomon error code is determined using an appropriate function call. In Lines 08-09, the data may be formatted. In Line 10, the formatted data is provided as a variable of a programmatic function call to generate the machine-readable identifier 133 in an image or other appropriate format.

Turning now to FIG. 9, shown is another example of the client application 130 importing data from an external source. As noted above, in some circumstances, input data provided by a user of the client application 130 may be manipulated on the reader device 109 or other device with access to the decrypted information. For example, a doctor may update or alter the data to include an up-to-date blood pressure reading, weight measurement, glucose level measurement, or other information. The user may wish to store this updated information on his or her client device 106 to maintain a more complete and accurate medical history. In some embodiments, the reader application 136 can generate a document 900 capable of printing for insertion into a physical medical file.

The reader application 136 may utilize its cryptographic key 121 to generate the document 900 having the machine-readable identifier 133a . . . 133b. The key management application 118 can provide the client device 106 with a suitable cryptographic key 121 based on the reader device 109, or other device, that generated the machine-readable identifier 133. The client application 130 can facilitate the capture of one or more images of the machine-readable identifier 133 positioned on the document 900. Once an image of the machine-readable identifier 133 is obtained on the client device 106 and decrypted, the client device 106 can update locally stored information and/or automatically populate fields in a user interface 131 for review by the user.

In various embodiments, the underlying data of the machine-readable identifier 133 generated by the reader application 136 is encrypted using a cryptographic key 121 only available to the client device 106 and the reader device 109. The client application 130 can decrypt the underlying data and store the data locally on the client device 106. If the user performs parts of ingestion process, the updated data may be provide in automatically populated fields in the user interface 131.

Multiple security mechanisms are built into the code and implementation of the client application 130. Because of the breadth of the potentially critical information, in various embodiments, this information is stored locally on the client device 106. Thus, the potential loss of this information through the "cloud" is reduced or eliminated. In various embodiments, the client application 130 may be integrated with cloud-based systems for the remote input and updating of information.

In addition to default password protection provided on smartphones or other types of client devices 106, an additional password or personal identifier number (PIN) may be required to access features of the client application 130. An incorrect password given a predefined number times consecutively (e.g., five times) may result in disabling use of the client application for a predefined period of time, such as twenty-four hours. Prior to sharing of this information electronically, an additional identifier representing the permission of the owner to share this information may be required.

In various embodiments, healthcare providers permitted to withdraw the information from the machine-readable identifier 133 may also be permitted to update or augment the information and provide the updated or augmented information back to the owner in the form of another machine-readable identifier 133. As a result, updated information can be reconciled with the information already present on the client device 106. In this fashion, the owner will not have to input new information as it will be completed by the client application 130. This can also include reminders for future visits that will incorporate into the mobile device calendar, reminders for medication refills, etc. In another example, the client application 130 can electronically reconcile medications with a pharmacy.

The client application 130 can be embodied in multiple versions, where each version uses a different language, such as English, Spanish, French, or other language. The user input may be translated from a language of the user to a language of the recipient by the translator service 120, if needed. This may occur prior to encoding the data for use in the machine-readable identifier 133 or upon decoding the information with the reader application 136. For those situations when a higher level of communication, or medical terminology in English is not known, this information used to assist in a medical or other type of assessment.

In one embodiment, a machine-readable identifier 133 may be encoded in a "lock screen" of a client device 106 so that a person without access to the phone may gain access to crucial identifying, health, or contact information without having to unlock the client device 106. In other embodiments, the information provided during an ingestion process may be periodically erased on the client device 106 or on the reader device 109, for example, at the end of a session of use.

Figure 10:
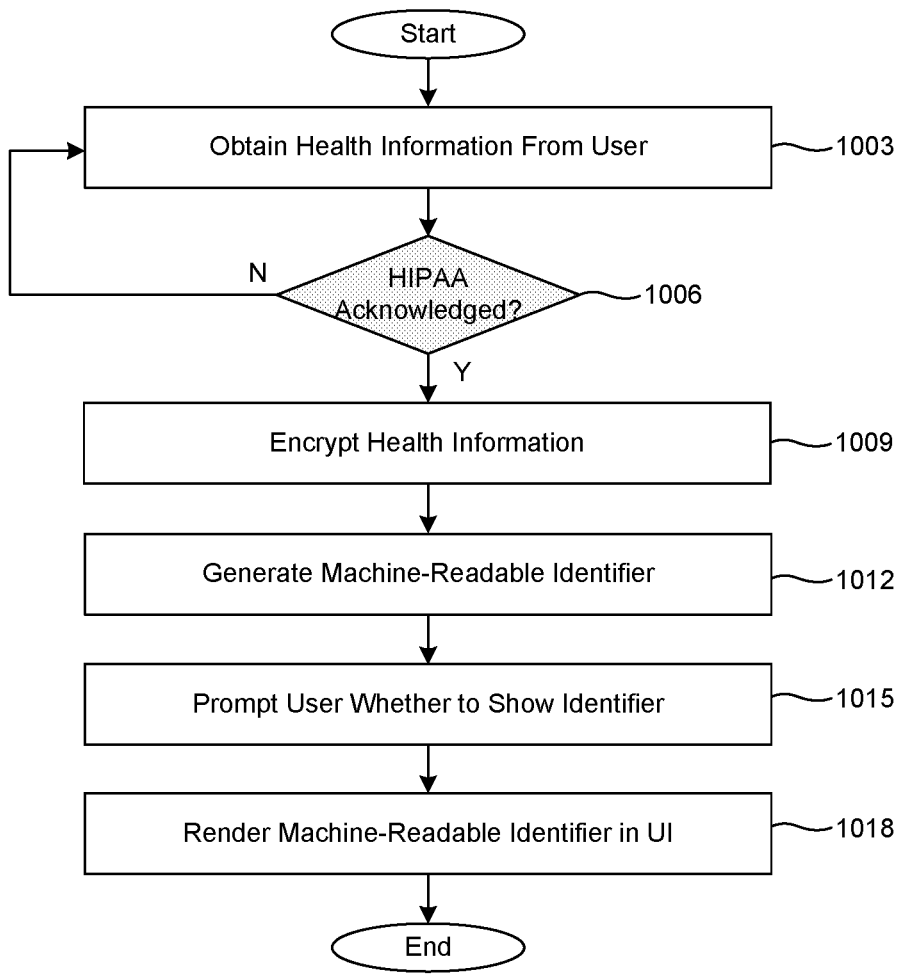
FIGS. 10-12 are flowcharts illustrating functionality of a client application executed in a client device according to various embodiments.

Referring next to FIG. 10, shown is a flowchart that provides one example of the operation of a portion of the client application 130 according to various embodiments. It is understood that the flowchart of FIG. 10 provides merely an example of the many different types of functional arrangements that may be employed to implement the operation of the portion of the client application 130 as described herein. As an alternative, the flowchart of FIG. 10 may be viewed as depicting an example of elements of a method implemented in the client device 106 according to one or more embodiments.

Starting with step 1003, the client application 130 is executed to obtain information, such as health information, from a user for one or more individuals, such as dependent persons, pets or other animals, etc. This may be accomplished using the user interfaces 131 which are presented subsequently in an ingestion process where a user iterates through the user interfaces 131 during one or more sessions. Next, in step 1006, the client application 130 determines whether a HIPAA notification has been acknowledged by the user. If the HIPAA notification has not been acknowledged, the HIPAA notification may be represented to the user and the process may revert back to 1003 or proceed to end. If the HIPAA notification has been acknowledged by the user, the process may proceed to 1009 where the general, health, or other information provided by the user is encrypted according to one or more predefined encryption standards and formats.

In various embodiments, the data is encrypted using one or more cryptographic keys 121. In various embodiments, the cryptographic key 121 comprises information provided by the user, such as a date of birth, a last name, a first name, a social security number, a combination thereof, or other potentially unique information. In 1012, the encrypted information is used to generate a machine-readable identifier 133, such as a barcode or a matrix code. The steps taken to generate the machine-readable identifier are described with respect to FIG. 6 and FIG. 8.

Referring back to FIG. 10, in step 1015, the user may be prompted with an additional notification asking the user whether the user desires to show the generated machine-readable identifier 133 on the client device display 124. Finally, in step 1018, the machine-readable identifier may be encoded in a user interface 131 for rendering in the client device display 124. At this point, the user may be able to provide the machine-readable identifier 133 for scanning by a reader device 109 or the user may print a document containing the information and having the machine-readable identifier 133 located thereon.

Figure 11:
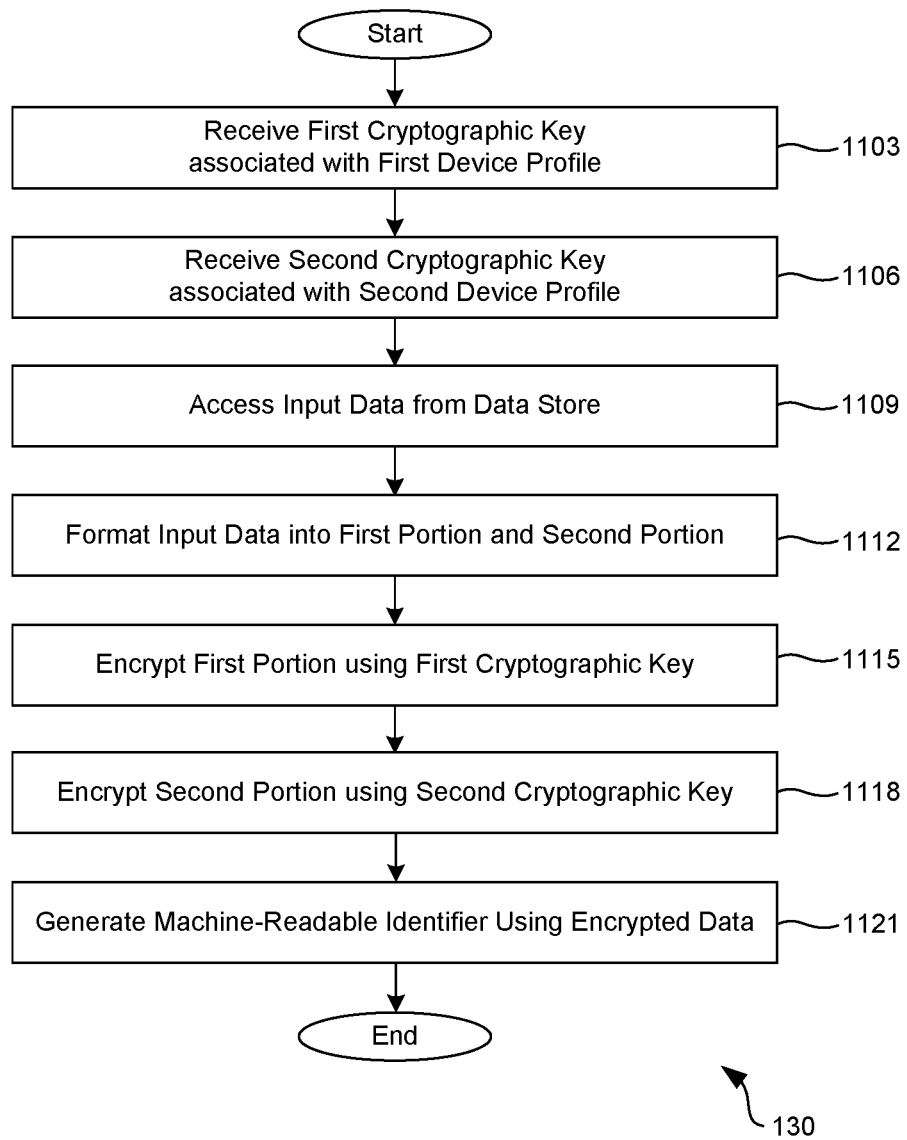

Referring next to FIG. 11, shown is a flowchart that provides another example of the operation of a portion of the client application 130 according to various embodiments. It is understood that the flowchart of FIG. 11 provides merely an example of the many different types of functional arrangements that may be employed to implement the operation of the portion of the client application 130 as described herein. As an alternative, the flowchart of FIG. 11 may be viewed as depicting an example of elements of a method implemented in the client device 106 according to one or more embodiments.

Starting at step 1103, a client application 130 executable on a client device 106 may be configured to access a first cryptographic key 121a associated with a first device profile 148a. Similarly, at step 1106, the client application 130 may access a second cryptographic key 121b associated with a second device profile 148b received over the network 112. As may be appreciated, the first cryptographic key 121 a and the second cryptographic key 121 b may be sent to the client device 106 by the key management application 118 or other similar service over the network 112. The first cryptographic key 121a and the second cryptographic key 121b may be provided to the client application 130 in response to a selection of a certain entity or organization, such as a medical office or medical professional. In one example, the first cryptographic key 121a is associated with a first medical provider. The first medical provider may own or operate a first reader device 109a associated with the first device profile 148a and having the first cryptographic key 121a stored thereon. Similarly, the second cryptographic key 121b is associated with a second medical provider, whereby the second medical provider may own or operate a second reader device 109b associated with the second device profile 148b and having the second cryptographic key 121b stored thereon.

As the client application 130 facilitates the collection of input data from a user through an ingestion process, in step 1109, the input data can be accessed for inclusion in a machine-readable identifier 133. The ingestion process may include a series of user interfaces 131 that prompt the user to enter a variety of data, such as those shown in FIGS. 7A-7K. In step 1112, the client application 130 may segment, partition, or otherwise format the input data into at least a first portion of data and a second portion of data. For example, the first portion of data may be capable of being interpreted by a device for a general practitioner while the second portion of data may be capable of being interpreted by a device for a chiropractor.

Next, in step 1115, the client application 130 may encrypt the first portion of data using the first cryptographic key 121 a while, in step 1118, the client application 130 may encrypt the second portion of data using the second cryptographic key 121b. The key management application 118 operating in the computing environment 103 may oversee the transmission and receipt of cryptographic keys 121 capable of decrypting the data, as authorized by the user. Alternatively, in other embodiments, a reader device 109 may be associated with a predefined cryptographic key 121 stored in the data store 115 of the computing environment 103. The key management application 118 can provide the client application 130 with a cryptographic key 121 for a particular reader device 109 so that the information is encrypted for access by the reader device 109 or other client device 106.

In step 1121, the client application 130 may generate a machine-readable identifier 133 using the first portion of data as encrypted and the second portion of data as encrypted for rendering in the client device display 124. The reader device 109 can capture one or more images of the machine-readable identifier 133 to access the underlying data.

In further embodiments, a user of the client application 130 may associate a device profile 148, such as one pertaining to a general practitioner, with a high level of access, where the general practitioner is able to use his or her reader device 109 to access all or a substantial amount of the input data provided by the user of the client application 130. The key management application 118 can send a cryptographic key 121 to the reader device 109 for the general practitioner as well as to the client device 106 for the user. Similarly, the key management application 118 can send a different cryptographic key 121 to a reader device 109 for the chiropractor or other medical provider. The client application 130 may encode data authorized for receipt by the general practitioner using a cryptographic key 121 corresponding to the reader device 109 of the general practitioner while encoding data authorized for receipt by the chiropractor using a different cryptographic key 121 for a reader device 109 of the chiropractor. To this end, using a single machine-readable identifier 133, access control to the underlying data of the machine-readable identifier 133 is provided. Thereafter, the process proceeds to terminate.

In some embodiments, a first access level 152a associated with the first portion of data may be defined. For example, a user can associate a required low access level 152 with his personal information while associating a required high access level 152 with his medical history. A reader devices 109 associated with a high access level 152 may access both the medical history and the personal information while a reader device 109 associated with a low access level 152 may only access the personal information. In one example, a coach of a child may have a low access level 152 granted to a client device 106 used to access emergency contact information for a player, as authorized by the player or parent.

In other words, the access level 152 may be used to determine which portions of the data the reader devices 109 can access. The user can also define through the client application 130 which entities, such as medical offices, have access to data associated with various access levels 152. To this end, a first access level 152a associated with the first portion of data and a second access level 152b associated with the second portion of data may be identified where the first portion of data will be encrypted using the first cryptographic key 121a based at least in part on the first access level 152a, and the second portion of data will be encrypted using the second cryptographic key 121b based at least in part on the second access level 152b. As may be appreciated, the first access level 152a may be different than the second access level 152b.

Figure 12:
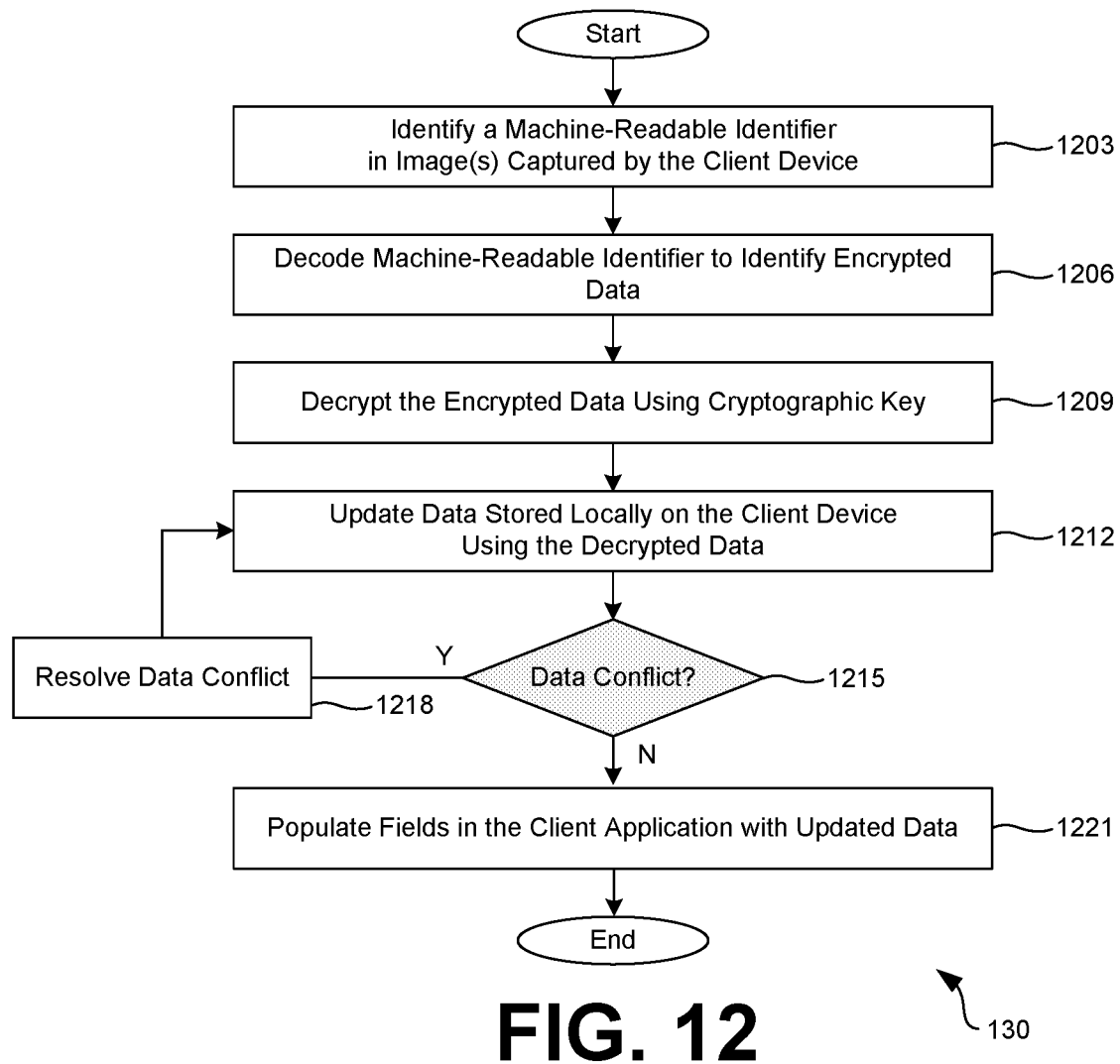

Referring next to FIG. 12, shown is a flowchart that provides another example of the operation of a portion of the client application 130 according to various embodiments. It is understood that the flowchart of FIG. 12 provides merely an example of the many different types of functional arrangements that may be employed to implement the operation of the portion of the client application 130 as described herein. As an alternative, the flowchart of FIG. 12 may be viewed as depicting an example of elements of a method implemented in the client device 106 according to one or more embodiments.

Starting with 1203, the client application 130 may identify a machine-readable identifier 133 in an image captured by a camera or other imaging device in communication with the client device 106. For example, the machine-readable identifier 133 may be one generated by the reader device 109 to provide updated, supplemented, or other manipulated data initially provided by a user of the client application 130 using an initial machine-readable identifier 133 generated after completion of an ingestion process. As may be appreciated, the data modified by the reader device 109 may be obtained from an original machine-readable identifier 133 generated on the client device 106. An image of the machine-readable identifier 133 may be obtained by the client device 106 to update its locally stored data. The image may be captured from the reader device display 127, as shown in FIG. 2, a display of another client device 106, or from a document 900, as shown in FIG. 9.

Next, in step 1206, the machine-readable identifier 133 is decoded to identify an amount of encrypted data. In step 1209, the client application 130 may decrypt the amount of encrypted data using a cryptographic key 121 associated with a device profile 148 from an originating device from which the machine-readable identifier 133 is obtained. In some embodiments, an amount of data read from the machine-readable identifier 133 may be public (not encrypted) that identifies the reader device 109 from which the machine-readable identifier 133 was obtained where any device can decode the amount of data. The amount of data may comprise a device identifier 145 and/or a unique identifier that identifies a person or client device 106 authorized to access the encrypted data. The client application 130 can communicate the device identifier 145 to the computing environment 103 to obtain a cryptographic key 121 if the client device 106 is so authorized.

In step 1212, the decrypted data obtained from the machine-readable identifier 133 may be used to update or supplement the data stored locally on the client device 106. In some situations, the decrypted data may conflict with data provided by the user. For example, portions of the data provided by the user to the reader device 109 through a first machine-readable identifier 133 may have been changed. Alternatively, the data provided by the user may be augmented with readings taken by a doctor that may have been previously unknown to the user.

Accordingly, in step 1215, the client application 130 determines whether a conflict exists between the decrypted data and the data provided by the user, for example, through the ingestion process. The data may conflict, for example, if the data provided by the user using his or her client device 106 is different than the data returned by the reader device 106 in any respect. For example, using the reader device 109, a physician or nurse may update the data provided by the user to reflect recent readings or measurements. Alternatively, using the reader device 109, the physician or nurse may augment the data provided by the user. In either scenario, a conflict between the data is identified as both sets of data are not identical. A DIFF function or similar function may be employed to identify specific portions of the data where conflicts exist.

If a conflict between the data exists, the process proceeds to step 1218 to reconcile or otherwise resolve the data conflict. In some embodiments, the user may be presented with information pertaining to the conflict where the user can select whether to keep the original data provided by the user or to update the data with the data provided from the reader device 109. In other embodiments, the data provided from the reader device 109 may automatically replace data provided by a user or automatically be added to the memory of the client device 106 to augment the data provided by the user during the ingestion process.

In some examples, some portions data may be associated with varying access levels 152 pertaining to particular types of data. For example, if a medical provider updates medical data stored on the client device 106, deference may be shown to the medical provider over the user as the medical provider may be assigned a high access level 152 by the user (or by default). In another example, if a medical provider updates personal information, such as a phone number or address for the user of the client device 106, deference may be shown to the user as he or she is likely situated to better understand his or her own number or address. In other words, the medical provider may have a high access level 152 for medical information and a low access level 152 for personal information.

Alternatively, if a data conflict does not exist, the process proceeds to step 1221 where, during future ingestion processes, the fields in the user interfaces 131 may be automatically populated with data obtained from the machine-readable identifier 133. Thereafter, the process proceeds to terminate.

Figure 13:
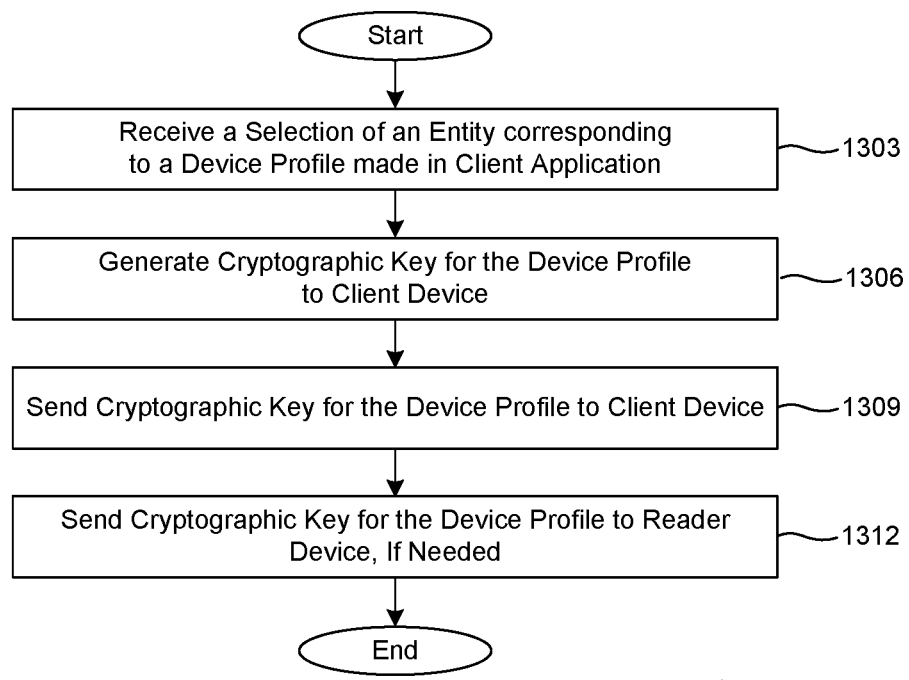
FIGS. 13 and 14 are flowcharts illustrating functionality of a remote application executed in a computing environment according to various embodiments.

With reference to FIG. 13, shown is a flowchart that an example of the operation of a portion of the key management application 118 according to various embodiments. It is understood that the flowchart of FIG. 13 provides merely an example of the many different types of functional arrangements that may be employed to implement the operation of the portion of the key management application 118 as described herein. As an alternative, the flowchart of FIG. 13 may be viewed as depicting an example of elements of a method implemented in the computing environment 103 according to one or more embodiments.

Starting with 1303, a selection of an entity, such as a medical provider, is received from a client device 106 where the selection was made in a client application 130. For example, the user can specify an entity for which he or she wants to share the input data provided during the ingestion process. In one example, the user can select "Atlanta Health" provider in a user interface 131 generated by the client application 130. "Atlanta Health" may own or operate one or more reader devices 109 which are associated with one or more device profiles 148 stored in the data store 115.

In some examples, an entity, or a device profile 148 corresponding to a reader device 109 operated by the entity, may have a predefined cryptographic key 121 stored in the data store 115. However, in step 1306, a cryptographic key 121 can be generated for the device profile 148, for example, to create a cryptographic key 121 unique to the user-to-entity relationship. As may be appreciated, step 1306 may be optional. In some examples, the cryptographic key 121 is generated pseudo-randomly, using information provided by the user, or a combination thereof.

Next, in step 1309, the cryptographic key 121 is sent to the client device 106 so that the client application 130 can encode the input data for receipt by the reader device 109 associated with the device profile 148. If the reader device 109 does not have the cryptographic key 121 stored thereon, in step 1312, the cryptographic key 121 may be sent to the reader device 109, if needed.

Figure 14:
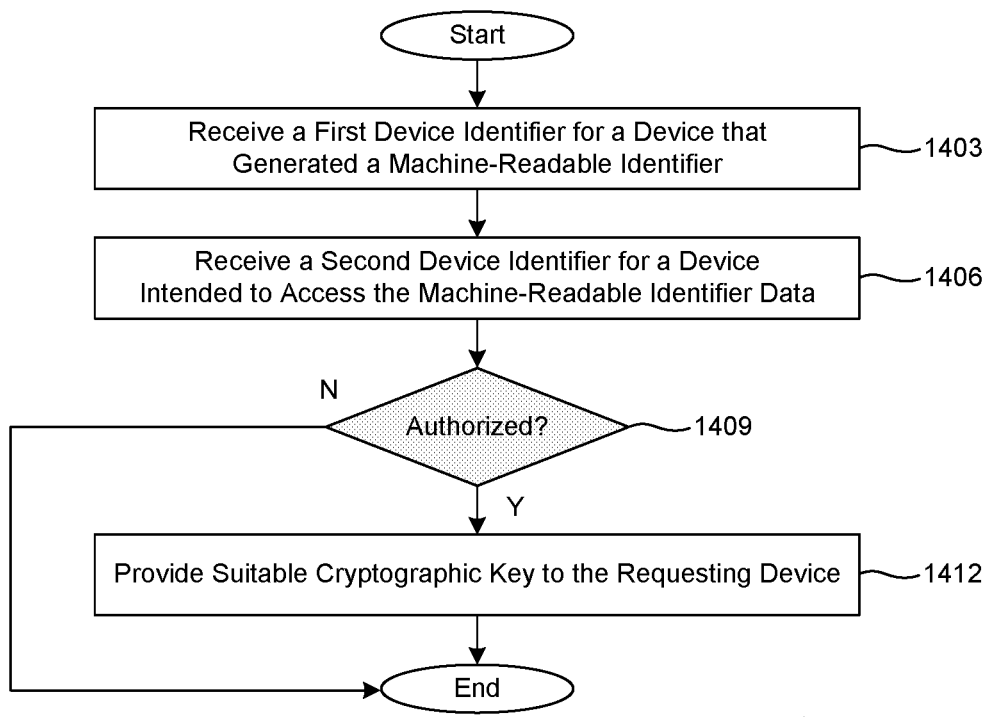

With reference to FIG. 14, shown is a flowchart that shows another example of the operation the key management application 118 according to various embodiments. It is understood that the flowchart of FIG. 14 provides merely an example of the many different types of functional arrangements that may be employed to implement the operation of the portion of the key management application 118 as described herein. As an alternative, the flowchart of FIG. 14 may be viewed as depicting an example of elements of a method implemented in the computing environment 103 according to one or more embodiments.

In some embodiments, the machine-readable identifier 133 may comprise non-encrypted data or data that may be decrypted using a global or shared cryptographic key 121. The data may include a first device identifier 145a for an originating device and a second device identifier 145b for an intended recipient. For example, a client application 130 can generate a machine-readable identifier 133 that includes a first device identifier 145a for the client device 106 that generated the machine-readable identifier 133a and a second device identifier 145b for an intended recipient reader device 109 associated with a particular entity, such as a selected medical provider.

When a reader device 109 scans the machine-readable identifier 133, it may determine whether it has access to the underlying data by analyzing the first device identifier 145a or the second device identifier 145b for the intended recipient. In other examples, the reader device 109 may communicate the device identifiers 145 to the key management application 118 for remote authorization. To this end, in step 1403, the key management application 118 may receive a first device identifier 145a for a device that generated a machine-readable identifier 133. Similarly, in step 1406, the key management application 118 may receive a second device identifier 145b for a device intended to access the underlying data of the machine-readable identifier 133.

Using the first device identifier 145a and the second device identifier 145b, the key management application 118 may determine, in step 1409, whether the device requesting a cryptographic key 121 to decrypt the underlying data of the machine-readable identifier 133 is authorized to access the underlying data by the originating user (e.g., the user of the client application 130 or the medical provider). If the requesting device is authorized to access the underlying data, in step 1412, the key management application 118 may send the cryptographic key 121 to the device, wherein the cryptographic key 121 is capable of decrypting the data encoded in the machine-readable identifier 133. Thereafter, the process proceeds to terminate. Referring back to step 1409, if the requesting device is not authorized to access the underlying data of the machine-readable identifier 133, the process proceeds to terminate.

The applications described herein, such as the client application 130, the reader application 136, and the key management application 118, provide the ability to effectively acquire, store, and reproduce vital information, such as information required at an initial visit or subsequent visit with a healthcare provider. Specifically, the present disclosure describes a client application 130 for obtaining a medical history in a user-friendly fashion and generating a machine-readable identifier 133 comprising the obtained medical history as encoded and encrypted data. In various embodiments, the information provided by a user via the client application 130 may be stored locally on the client device 106. The information stored on the client device 106 may be encrypted for local storage. Additionally, at return visits, any changes to the health history can be easily identified and provided to the provider.

Today, existing health-related applications are focused towards assisting an individual in increasing their ability to take responsibility for their own care, promoting healthy living, and linking with electronic medical records systems specific to a provider or institution in order to obtain tests and lab results. These applications include various degrees of daily, or at best, weekly data points that need to be updated in order to justify use of the client application 130.

The client application 130 and the reader application 136 may be implemented on the iOS®, Blackberry®, Linux®, Android®, Windows®, and/or other suitable operating systems. The information obtained by the client application 130 only needs to be provided by a user once and only updated with significant and relevant changes (e.g., medication changes, surgical procedures) which will only be necessary infrequently for the majority of patients. In addition, the client application 130 allows a user to provide vital information for dependents or those whom the user may be responsible. As may be appreciated, the value of easily and correctly providing basic information is enormous.

According to various embodiments, a focused, low-maintenance, and specific account of essential medical information is obtained that is required by healthcare providers and other entities to provide necessary routine care. This information is generated by physicians with physicians in mind, but created for an easy navigation of the system. The work flow will be created in a way that navigation can be completed by all individuals with just a basic literacy level. In various embodiments, the breadth of information required from a user may pivot on a predefined number of questions (e.g., seven questions or some other number) that may be vital for all initial visits to any healthcare provider. In various embodiments, these questions may be specific and not open ended.

The client application 130 generates a series of one or more user interfaces 131 to obtain information from the user. Further, the client application 130 correlates the information into an easy and legible form for both the physician and the patient. This also allows for efficient transfer of basic medical information between various providers, such as general physicians and specialists. The client application 130 facilitates a correlation of medical history or other information for relatives or other individuals, such as parents, children, pets, etc. For example, the information provided by another may be beneficial in situations where patients are unable to provide their own history due to pain, stress, confusion, loss of consciousness, etc., as well as times when a parent is distracted due to an emergency situation. In these instances, this vital information can be effectively communicated quickly, easily, and accurately, thereby preventing medical errors due to lack of accurate and complete information. Further, the client application 130 is configured to improve healthcare for those individuals with communication disabilities, such as those who are hearing impaired or mute.

In various embodiments, a doctor's office or other healthcare provider may designate information as being required or optional during a client intake. The client application 130 is executed to collect data points designated as being required by the healthcare providers. This information may be encrypted in accordance with HIPAA and Health Information Technology for Economic and Clinical Health Act ("HITECH") regulations, and may be made accessible to the user or to specified healthcare providers using a key or a password.

According to various embodiments, the information collected may be limited to the following: past medical history, past surgical history, allergies, medications, family history, social history, and immunizations although, in other embodiments, additional information may be collected. The client application 130 may assist the user in providing correct spelling for basic medical terms and medications to prevent confusion and incorrect documentation that can lead to medical errors.

The information collected by the client application 130 may be organized in a summary screen shown in a user interface 131 for reference while filling out new patient information packages. In various embodiments, this information may be converted into a Microsoft Word® or PDF format for printing prior to visit with a healthcare provider. Finally, this information may be encrypted and the encrypted information may be converted into a matrix code or other machine-readable identifier 133 for a paperless and wireless transfer of information directly to a healthcare provider. In various embodiments, a scan of the machine-readable identifier 133 causes an automatic population of the underlying information into a database of various electronic medical record systems.

In addition to collecting personal information, the client application 130 may be configured to obtain health information for dependents, family members, pets etc. This may assist in providing healthcare professionals with complete and accurate information when dependents and family members are unable to provide this information themselves due to age, incapacity, etc. This may help the healthcare provider accurately assess patients, streamline care, and prevent medical errors due to incomplete medical histories. As noted above, the client application 130 may be configured to obtain information about pets, as their medical history is also valuable to owners and veterinarians. By being able to easily reference this information in the same platform as the user of the client application 130, the information can be used for school, college, international travel, emergencies, and other situations.

Although this disclosure provides multiple examples in context of healthcare data, the embodiments enclosed herein are applicable across many industries. For example, the health information can include information pertaining to an automobile. The mechanic can view service records by scanning a machine-readable identifier 133 presented on a client device 106, which can include a person's smartphone or a computing device of the automobile.

With reference to FIG. 15, shown is a schematic block diagram of the computing environment 103 according to an embodiment of the present disclosure. The computing environment 103 includes one or more computing devices 1500. Each computing device 1500 includes at least one processor circuit, for example, having a processor 1503 and a memory 1506, both of which are coupled to a local interface 1509. To this end, each computing device 1500 may comprise, for example, at least one server computer or like device. The local interface 1509 may comprise, for example, a data bus with an accompanying address/control bus or other bus structure as can be appreciated.

Stored in the memory 1506 are both data and several components that are executable by the processor 1503. In particular, stored in the memory 1506 and executable by the processor 1503 are the key management application 118, the translator service 120, the direct messaging service 122, and other computing environment applications. Also stored in the memory 1506 may be the data store 115 and other data. In addition, an operating system 1512 may be stored in the memory 1506 and executable by the processor 1503. It is understood that there may be other applications that are stored in the memory 1506 and are executable by the processor 1503 as can be appreciated.

With reference to FIG. 16, shown is a schematic block diagram of the client device 106 according to an embodiment of the present disclosure. Each client device 106 includes at least one processor circuit, for example, having a processor 1603 and a memory 1606, both of which are coupled to a local interface 1609. To this end, each client device 106 may comprise, for example, a smartphone, a tablet, a personal computer, or other similar device. The local interface 1609 may comprise, for example, a data bus with an accompanying address/control bus or other bus structure as can be appreciated.

Stored in the memory 1606 are both data and several components that are executable by the processor 1603. In particular, stored in the memory 1606 and executable by the processor 1603 are the client application 130 and other applications. Also stored in the memory 1606 may be a client data store 1612 (also referred to herein as a local data store) and other data. In addition, a client operating system 1615 may be stored in the memory 1606 and executable by the processor 1603. It is understood that there may be other applications that are stored in the memory 1606 and are executable by the processor 1603 as can be appreciated.

With reference to FIG. 17, shown is a schematic block diagram of the reader device 109 according to an embodiment of the present disclosure. Each reader device 109 includes at least one processor circuit, for example, having a processor 1703 and a memory 1706, both of which are coupled to a local interface 1709. To this end, each reader device 109 may comprise, for example, a smartphone, a tablet, a personal computer, or other similar device. The local interface 1709 may comprise, for example, a data bus with an accompanying address/control bus or other bus structure as can be appreciated.

Stored in the memory 1706 are both data and several components that are executable by the processor 1703. In particular, stored in the memory 1706 and executable by the processor 1703 are the reader application 136 and other applications. Also stored in the memory 1706 may be a reader data store 1712 and other data. In addition, a client operating system 1715 may be stored in the memory 1706 and executable by the processor 1703. It is understood that there may be other applications that are stored in the memory 1706 and are executable by the processor 1703 as can be appreciated.

Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, Swift®, or other programming languages.

A number of software components are stored in the memory executable by the processors. In this respect, the term "executable" means a program file that is in a form that can ultimately be run by the processors. Examples of executable programs may be, for example, a compiled program that can be translated into machine code in a format that can be loaded into a random access portion of the memory and run by a processor, source code that may be expressed in proper format such as object code that is capable of being loaded into a random access portion of memory and executed by a processor, source code that may be interpreted by another executable program to generate instructions in a random access portion of the memory to be executed by a processor, etc. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory is defined herein as including both volatile and nonvolatile memory and data storage components. Volatile components are those that do not retain data values upon loss of power. Nonvolatile components are those that retain data upon a loss of power. Thus, the memory may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor may represent multiple processors and/or multiple processor cores and the memory may represent multiple memories that operate in parallel processing circuits, respectively. In such a case, the local interface may be an appropriate network that facilitates communication between any two of the multiple processors, between any processor and any of the memories, or between any two of the memories, etc. The local interface may comprise additional systems designed to coordinate this communication, including, for example, performing load balancing. The processor may be of electrical or of some other available construction.

Although the client application 130, the reader application 136, the key management application 118, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts of FIGS. 6 and 10-14 show the functionality and operation of an implementation of portions of the client application 130, the reader application 136, and the key management application 118. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor in a computer system or other system. The machine code may be converted from the source code, etc. If embodied in hardware, each block may represent a circuit or a number of interconnected circuits to implement the specified logical function(s).

Although the flowcharts of FIGS. 6 and 10-14 show a specific order of execution, it is understood that the order of execution may differ from that which is depicted. For example, the order of execution of two or more blocks may be scrambled relative to the order shown. Also, two or more blocks shown in succession in FIGS. 6 and 10-14 may be executed concurrently or with partial concurrence. Further, in some embodiments, one or more of the blocks shown in FIGS. 6 and 10-14 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the client application 130, the reader application 136, and the key management application 118 that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, the client application 130, the reader application 136, and the key management application 118 may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 1500 or in multiple computing devices in the same computing environment 103. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system, comprising:
    a client device comprising at least one hardware processor;
    a client application executable in the client device comprising program instructions that, when executed, cause the client device to:
        generate a first machine-readable identifier using a first amount of data encrypted using at least one cryptographic key for rendering in a display of the client device, wherein a reader device having the at least one cryptographic key stored thereon is configured to decrypt the data;
        identify a second machine-readable identifier in at least one image captured by the client device;
        decode the second machine-readable identifier to identify a second amount of data encrypted by the reader device using the at least one cryptographic key;
        decrypt the second amount of data using the at least one cryptographic key; and
        identify whether a conflict exists between the first amount of data and the second amount of data.

2. The system of claim 1, wherein the client application further comprises program instructions that, when executed, cause the client device to, in response to the conflict existing between the first amount of data and the second amount of data, perform a task to resolve the conflict.

3. The system of claim 1, wherein the conflict is identified in response to the reader device altering the first amount of data to generate the second amount of data.

4. The system of claim 2, wherein the task comprises:
    presenting information associated with the conflict in a user interface of the client application;
    receiving a selection of the first amount of data or the second amount of data in the user interface; and
    in response to the selection, updating a data store of the client device with the first amount of data as selected or the second amount of data as selected.

5. The system of claim 2, wherein the task comprises updating a data store of the client device with the second amount of data.

6. The system of claim 1, wherein the client application further comprises program instructions that, when executed, cause the client device to populate at least one field of a user interface in the client application with at least a portion of the second amount of data.

7. The system of claim 1, wherein the first amount of data encrypted using at least one cryptographic key further comprises a first portion of user input and a second portion of user input obtained during an ingestion process, the first portion of user input being encrypted using a first cryptographic key accessible by the reader device and the second portion of user input being encrypted using a second cryptographic key not accessible by the reader device.

8. The system of claim 1, wherein the machine-readable identifier is a quick-response (QR) code or a bar code.

9. The system of claim 1, wherein the client application further comprises program instructions that, when executed, cause the client device to receive at least one cryptographic key from a remote application executing in a remote computing environment over a network.

10. The system of claim 9, wherein the remote application executing in the remote computing environment is configured to send the at least one cryptographic key to the reader device over the network.

11. A computer-implemented method, comprising:
    generating, by a client device comprising at least one hardware processor, a first machine-readable identifier using a first amount of data encrypted using at least one cryptographic key for rendering in a display of the client device, wherein a reader device having the at least one cryptographic key stored thereon is configured to decrypt the data;
    identifying, by the client device, a second machine-readable identifier in at least one image captured by the client device;
    decoding, by the client device, the second machine-readable identifier to identify a second amount of data encrypted by the reader device using the at least one cryptographic key;
    decrypting, by the client device, the second amount of data using the at least one cryptographic key; and
    identifying, by the client device, whether a conflict exists between the first amount of data and the second amount of data.

12. The computer-implemented method of claim 11, further comprising, in response to the conflict existing between the first amount of data and the second amount of data, performing, by the client device, a task to resolve the conflict.

13. The computer-implemented method of claim 11, wherein the conflict is identified in response to the reader device altering the first amount of data to generate the second amount of data.

14. The computer-implemented method of claim 12, wherein the task comprises:
    presenting, by the client device, information associated with the conflict in a user interface of a client application;
    identifying, by the client device, a selection of the first amount of data or the second amount of data made in the user interface; and
    in response to the selection being identified, updating, by the client device, a data store of the client device with the first amount of data as selected or the second amount of data as selected.

15. The computer-implemented method of claim 12, wherein the task comprises updating, by the client device, a data store of the client device with the second amount of data.

16. The computer-implemented method of claim 11, further comprising populating, by the client device, at least one field of a user interface in a client application with at least a portion of the second amount of data.

17. The computer-implemented method of claim 11, wherein the first amount of data encrypted using at least one cryptographic key further comprises a first portion of user input and a second portion of user input obtained during an ingestion process, the first portion of user input being encrypted using a first cryptographic key accessible by the reader device and the second portion of user input being encrypted using a second cryptographic key not accessible by the reader device.

18. The computer-implemented method of claim 11, wherein the machine-readable identifier is a quick-response (QR) code or a bar code.

19. The computer-implemented method of claim 11, further comprising receiving, by the client device, at least one cryptographic key from a remote application executing in a remote computing environment over a network.

20. The computer-implemented method of claim 19, wherein the remote application executing in the remote computing environment is configured to send the at least one cryptographic key to the reader device over the network.

* * * * *